US012208270B2

(12) United States Patent
Moffitt et al.

(10) Patent No.: US 12,208,270 B2
(45) Date of Patent: Jan. 28, 2025

(54) METHODS AND SYSTEMS FOR DEEP BRAIN STIMULATION OF THE NUCLEUS BASALIS OF MEYNERT

(71) Applicants: Boston Scientific Neuromodulation Corporation, Valencia, CA (US);
Augusta University Research Institute, Inc., Augusta, GA (US)

(72) Inventors: Michael A. Moffitt, Solon, OH (US);
David Blake, Martinez, GA (US)

(73) Assignees: Boston Scientific Neuromodulation Corporation, Valencia, CA (US);
Augusta University Research Institute, Inc., Augusta, GA (US)

( * ) Notice: Subject to any disclaimer, the term of this patent is extended or adjusted under 35 U.S.C. 154(b) by 383 days.

(21) Appl. No.: 17/680,034

(22) Filed: Feb. 24, 2022

(65) Prior Publication Data

US 2022/0266014 A1 Aug. 25, 2022

Related U.S. Application Data

(60) Provisional application No. 63/153,775, filed on Feb. 25, 2021.

(51) Int. Cl.
*A61N 1/36* (2006.01)
*A61N 1/05* (2006.01)

(52) U.S. Cl.
CPC ......... *A61N 1/3615* (2013.01); *A61N 1/0531* (2013.01); *A61N 1/0534* (2013.01);
(Continued)

(58) Field of Classification Search
None
See application file for complete search history.

(56) References Cited

U.S. PATENT DOCUMENTS

| 4,602,624 A | 7/1986 | Naples et al. |
| 4,630,611 A | 12/1986 | King |

(Continued)

FOREIGN PATENT DOCUMENTS

| EP | 0580928 A1 | 2/1994 |
| EP | 0650694 B1 | 7/1998 |

(Continued)

OTHER PUBLICATIONS

International Search Report and Written Opinion for PCT Application No. PCT/US2022/017739 mailed Jun. 1, 2022.

(Continued)

*Primary Examiner* — Michael W Kahelin
*Assistant Examiner* — Luke M Stanley
(74) *Attorney, Agent, or Firm* — Branch Partners PLLC;
Bruce E. Black

(57) ABSTRACT

A system for stimulation of a nucleus basalis of Meynert (NBM) of a patient includes an implantable electrical stimulation lead including electrodes and configured for implantation of at least one of the electrodes adjacent to or within the NBM of the patient; and an implantable pulse generator coupleable to the implantable electrical stimulation lead and configured for delivering electrical stimulation to the NBM through at least one of the electrodes of the implantable electrical stimulation lead, the implantable pulse generator including at least one processor configured to, upon user request, during an initial stimulation period, which is at least 1 month in duration and has a start and an end, increase over time at least one of a duration or an amplitude of the electrical stimulation from an initial value at the start of the initial stimulation period to a final value at the end of the initial stimulation period.

20 Claims, 9 Drawing Sheets

(52) U.S. Cl.
CPC ..... *A61N 1/36082* (2013.01); *A61N 1/36121* (2013.01); *A61N 1/36132* (2013.01); *A61N 1/36139* (2013.01); *A61N 1/36167* (2013.01)

(56) References Cited

U.S. PATENT DOCUMENTS

| | | | |
|---|---|---|---|
| 4,744,370 A | 5/1988 | Harris | |
| 5,000,194 A | 3/1991 | van den Honert et al. | |
| 5,070,605 A | 12/1991 | Daglow et al. | |
| 5,135,001 A | 8/1992 | Sinofsky et al. | |
| 5,348,481 A | 9/1994 | Ortiz | |
| 5,374,285 A | 12/1994 | Vaiani et al. | |
| 5,458,629 A | 10/1995 | Baudino et al. | |
| 5,522,874 A | 6/1996 | Gates | |
| 5,711,316 A | 1/1998 | Elsberry et al. | |
| 5,713,922 A | 2/1998 | King | |
| 5,800,350 A | 9/1998 | Coppleson et al. | |
| 5,843,148 A | 12/1998 | Gijsbers et al. | |
| 5,938,688 A | 8/1999 | Schiff | |
| 5,987,361 A | 11/1999 | Mortimer | |
| 6,018,684 A | 1/2000 | Bartig et al. | |
| 6,125,302 A | 9/2000 | Kuzma | |
| 6,134,478 A | 10/2000 | Spehr | |
| 6,161,047 A | 12/2000 | King et al. | |
| 6,162,101 A | 12/2000 | Fischer et al. | |
| 6,167,311 A | 12/2000 | Rezai | |
| 6,181,969 B1 | 1/2001 | Gord | |
| 6,295,944 B1 | 10/2001 | Lovett | |
| 6,305,962 B1 | 10/2001 | Maher et al. | |
| 6,322,559 B1 | 11/2001 | Daulton et al. | |
| 6,391,985 B1 | 5/2002 | Goode et al. | |
| 6,428,336 B1 | 8/2002 | Akerfeldt | |
| 6,510,347 B2 | 1/2003 | Borkan | |
| 6,516,227 B1 | 2/2003 | Meadows et al. | |
| 6,556,873 B1 | 4/2003 | Smits | |
| 6,564,078 B1 | 5/2003 | Marino et al. | |
| 6,609,029 B1 | 8/2003 | Mann et al. | |
| 6,609,032 B1 | 8/2003 | Woods et al. | |
| 6,663,570 B2 | 12/2003 | Mott et al. | |
| 6,678,564 B2 | 1/2004 | Ketterl et al. | |
| 6,741,892 B1 | 5/2004 | Meadows et al. | |
| 6,757,970 B1 | 7/2004 | Kuzma et al. | |
| 6,895,280 B2 | 5/2005 | Meadows et al. | |
| 7,027,852 B2 | 4/2006 | Helland | |
| 7,047,084 B2 | 5/2006 | Erickson et al. | |
| 7,108,549 B2 | 9/2006 | Lyu et al. | |
| 7,203,548 B2 | 4/2007 | Whitehurst et al. | |
| 7,241,180 B1 | 7/2007 | Rentas | |
| 7,244,150 B1 | 7/2007 | Brase et al. | |
| 7,292,890 B2 | 11/2007 | Whitehurst et al. | |
| 7,402,083 B2 | 7/2008 | Kast et al. | |
| 7,437,193 B2 | 10/2008 | Parramon et al. | |
| 7,450,997 B1 | 11/2008 | Pianca et al. | |
| 7,489,971 B1 | 2/2009 | Franz | |
| 7,668,601 B2 | 2/2010 | Hegland et al. | |
| 7,672,734 B2 | 3/2010 | Anderson et al. | |
| 7,736,191 B1 | 6/2010 | Sochor | |
| 7,761,165 B1 | 7/2010 | He et al. | |
| 7,761,985 B2 | 7/2010 | Hegland et al. | |
| 7,783,359 B2 | 8/2010 | Meadows | |
| 7,792,590 B1 | 9/2010 | Pianca et al. | |
| 7,798,864 B2 | 9/2010 | Barker et al. | |
| 7,809,446 B2 | 10/2010 | Meadows | |
| 7,822,482 B2 | 10/2010 | Gerber | |
| 7,840,188 B2 | 11/2010 | Kurokawa | |
| 7,848,802 B2 | 12/2010 | Goetz | |
| 7,856,707 B2 | 12/2010 | Cole | |
| 7,860,570 B2 | 12/2010 | Whitehurst et al. | |
| 7,949,395 B2 | 5/2011 | Kuzma | |
| 7,974,705 B2 | 7/2011 | Zdeblick et al. | |
| 7,974,706 B2 | 7/2011 | Moffitt et al. | |
| 7,979,140 B2 | 7/2011 | Schulman | |
| 8,000,808 B2 | 8/2011 | Hegland et al. | |
| 8,019,440 B2 | 9/2011 | Kokones et al. | |
| 8,036,755 B2 | 10/2011 | Franz | |
| 8,041,309 B2 | 10/2011 | Kurokawa | |
| 8,046,074 B2 | 10/2011 | Barker | |
| 8,099,177 B2 | 1/2012 | Dahlberg | |
| 8,100,726 B2 | 1/2012 | Harlan et al. | |
| 8,140,163 B1 | 3/2012 | Daglow et al. | |
| 8,175,710 B2 | 5/2012 | He | |
| 8,190,259 B1 | 5/2012 | Smith | |
| 8,224,450 B2 | 7/2012 | Brase | |
| 8,225,504 B2 | 7/2012 | Dye et al. | |
| 8,239,042 B2 | 8/2012 | Chinn et al. | |
| 8,271,094 B1 | 9/2012 | Moffitt et al. | |
| 8,295,944 B2 | 10/2012 | Howard et al. | |
| 8,301,255 B2 | 10/2012 | Barker | |
| 8,321,025 B2 | 11/2012 | Bedenbaugh | |
| 8,326,433 B2 | 12/2012 | Blum et al. | |
| 8,342,887 B2 | 1/2013 | Gleason et al. | |
| 8,359,107 B2 | 1/2013 | Pianca et al. | |
| 8,364,278 B2 | 1/2013 | Pianca et al. | |
| 8,391,985 B2 | 3/2013 | McDonald | |
| 8,483,237 B2 | 7/2013 | Zimmermann et al. | |
| 8,565,886 B2 | 10/2013 | Nelson et al. | |
| 8,583,237 B2 | 11/2013 | Bedenbaugh | |
| 8,675,945 B2 | 3/2014 | Barnhorst et al. | |
| 8,688,235 B1 | 4/2014 | Pianca et al. | |
| 8,831,731 B2 | 9/2014 | Blum et al. | |
| 8,831,742 B2 | 9/2014 | Pianca et al. | |
| 8,849,415 B2 | 9/2014 | Bedenbaugh | |
| 8,849,632 B2 | 9/2014 | Sparks et al. | |
| 8,958,615 B2 | 2/2015 | Blum et al. | |
| 8,968,331 B1 | 3/2015 | Sochor | |
| 9,101,775 B2 | 8/2015 | Barker | |
| 9,149,630 B2 | 10/2015 | Howard et al. | |
| 9,162,048 B2 | 10/2015 | Romero et al. | |
| 9,270,070 B2 | 2/2016 | Pianca | |
| 9,289,596 B2 | 3/2016 | Leven | |
| 9,352,147 B2 | 5/2016 | Nguyen-stella | |
| 9,381,348 B2 | 7/2016 | Romero et al. | |
| 9,403,022 B2 | 8/2016 | Ries et al. | |
| 9,409,032 B2 | 8/2016 | Brase et al. | |
| 9,415,154 B2 | 8/2016 | Leven | |
| 9,440,066 B2 | 9/2016 | Black | |
| 9,498,620 B2 | 11/2016 | Romero et al. | |
| 9,504,839 B2 | 11/2016 | Leven | |
| 9,555,234 B2 | 1/2017 | Duijsens et al. | |
| 10,576,283 B2 | 3/2020 | Flaherty et al. | |
| 2001/0023368 A1 | 9/2001 | Black et al. | |
| 2002/0156513 A1 | 10/2002 | Borkan | |
| 2002/0183817 A1 | 12/2002 | Van Venrooij et al. | |
| 2005/0015130 A1 | 1/2005 | Gill | |
| 2005/0038489 A1 | 2/2005 | Grill | |
| 2005/0171587 A1 | 8/2005 | Daglow et al. | |
| 2006/0025841 A1 | 2/2006 | McIntyre | |
| 2006/0247697 A1 | 11/2006 | Sharma et al. | |
| 2007/0060974 A1 | 3/2007 | Lozano et al. | |
| 2007/0150036 A1 | 6/2007 | Anderson | |
| 2007/0168007 A1 | 7/2007 | Kuzma et al. | |
| 2007/0203546 A1 | 8/2007 | Stone et al. | |
| 2007/0219551 A1 | 9/2007 | Honour et al. | |
| 2008/0077186 A1 | 3/2008 | Thompson et al. | |
| 2008/0103580 A1 | 5/2008 | Gerber | |
| 2008/0114230 A1 | 5/2008 | Addis | |
| 2008/0215125 A1 | 9/2008 | Farah et al. | |
| 2008/0255647 A1 | 10/2008 | Jensen et al. | |
| 2009/0054941 A1 | 2/2009 | Eggen et al. | |
| 2009/0187222 A1 | 7/2009 | Barker | |
| 2009/0204192 A1 | 8/2009 | Carlton et al. | |
| 2009/0248099 A1* | 10/2009 | Assaf | A61N 1/0534 607/45 |
| 2009/0276021 A1 | 11/2009 | Meadows et al. | |
| 2009/0287272 A1 | 11/2009 | Kokones et al. | |
| 2009/0287273 A1 | 11/2009 | Carlton et al. | |
| 2010/0030298 A1 | 2/2010 | Martens et al. | |
| 2010/0036468 A1 | 2/2010 | Decre et al. | |
| 2010/0057176 A1 | 3/2010 | Barker | |
| 2010/0070009 A1 | 3/2010 | Barker | |
| 2010/0070012 A1 | 3/2010 | Chinn et al. | |
| 2010/0076535 A1 | 3/2010 | Pianca et al. | |
| 2010/0077606 A1 | 4/2010 | Black et al. | |
| 2010/0082076 A1 | 4/2010 | Lee et al. | |

(56) References Cited

U.S. PATENT DOCUMENTS

| | | |
|---|---|---|
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0004267 A1 | 1/2011 | Meadows |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0245903 A1 | 10/2011 | Schulte et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071937 A1 | 3/2012 | Sundaramurthy et al. |
| 2012/0071949 A1 | 3/2012 | Pianca et al. |
| 2012/0116475 A1* | 5/2012 | Nelson ............... A61N 1/36082 607/45 |
| 2012/0165911 A1 | 6/2012 | Pianca |
| 2012/0197375 A1 | 8/2012 | Pianca et al. |
| 2012/0203302 A1 | 8/2012 | Moffit et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0232603 A1 | 9/2012 | Sage |
| 2012/0259386 A1 | 10/2012 | DeRohan et al. |
| 2012/0271376 A1 | 10/2012 | Kokones et al. |
| 2012/0314924 A1 | 12/2012 | Carlton et al. |
| 2012/0316615 A1 | 12/2012 | DiGiore et al. |
| 2013/0060305 A1 | 3/2013 | Bokil |
| 2013/0104066 A1 | 4/2013 | Soederstroem |
| 2013/0105071 A1 | 5/2013 | DiGiore et al. |
| 2013/0109254 A1 | 5/2013 | Klardie et al. |
| 2013/0116744 A1 | 5/2013 | Blum et al. |
| 2013/0116748 A1 | 5/2013 | Bokil et al. |
| 2013/0116929 A1 | 5/2013 | Carlton et al. |
| 2013/0184781 A1* | 7/2013 | Eskandar ............ A61N 1/36167 607/45 |
| 2013/0197424 A1 | 8/2013 | Bedenbaugh |
| 2013/0197602 A1 | 8/2013 | Pianca et al. |
| 2013/0197603 A1 | 8/2013 | Eiger |
| 2013/0261684 A1 | 10/2013 | Howard |
| 2013/0288501 A1 | 10/2013 | Russell et al. |
| 2013/0289667 A1* | 10/2013 | Wacnik ............... A61N 1/36171 607/2 |
| 2013/0304140 A1 | 11/2013 | Derohan et al. |
| 2013/0317573 A1 | 11/2013 | Zhu et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0066999 A1 | 3/2014 | Carcieri et al. |
| 2014/0067022 A1 | 3/2014 | Carcieri et al. |
| 2014/0088666 A1 | 3/2014 | Goetz et al. |
| 2014/0122379 A1 | 5/2014 | Moffitt et al. |
| 2014/0142671 A1 | 5/2014 | Moffitt et al. |
| 2014/0180375 A1 | 6/2014 | Pianca et al. |
| 2014/0200633 A1 | 7/2014 | Moffitt |
| 2014/0277284 A1 | 9/2014 | Chen et al. |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0066111 A1 | 3/2015 | Blum et al. |
| 2015/0066120 A1 | 3/2015 | Govea |
| 2015/0127063 A1 | 5/2015 | Datta |
| 2015/0151113 A1 | 6/2015 | Govea et al. |
| 2015/0283379 A1 | 10/2015 | Venkatesan |
| 2015/0360023 A1 | 12/2015 | Howard et al. |
| 2015/0374978 A1 | 12/2015 | Howard et al. |
| 2016/0001080 A9 | 1/2016 | Blum et al. |
| 2016/0030749 A1 | 2/2016 | Carcieri et al. |
| 2016/0059019 A1 | 3/2016 | Malinowski et al. |
| 2016/0067495 A1 | 3/2016 | Chaturvedi et al. |
| 2016/0114165 A1 | 4/2016 | Levine et al. |
| 2016/0129242 A1 | 5/2016 | Malinowski |
| 2016/0129265 A1 | 5/2016 | Malinowski |
| 2016/0228692 A1 | 8/2016 | Steinke et al. |
| 2016/0296745 A1 | 10/2016 | Govea et al. |
| 2016/0346557 A1 | 12/2016 | Bokil |
| 2016/0375248 A1 | 12/2016 | Carcieri et al. |
| 2016/0375258 A1 | 12/2016 | Steinke |
| 2017/0014635 A1 | 1/2017 | Villarta et al. |
| 2017/0143967 A1* | 5/2017 | Blake, Jr. ........... A61N 1/36089 |
| 2017/0143978 A1 | 5/2017 | Barker |
| 2017/0151436 A1* | 6/2017 | Flaherty ............... A61B 5/0531 |
| 2017/0225007 A1 | 8/2017 | Orinski |
| 2017/0259078 A1 | 9/2017 | Howard |
| 2017/0304633 A1 | 10/2017 | Zhang |
| 2018/0064930 A1 | 3/2018 | Zhang et al. |
| 2018/0078776 A1 | 3/2018 | Mustakos et al. |
| 2018/0110971 A1 | 4/2018 | Serrano Carmona |
| 2018/0185650 A1 | 7/2018 | Shah |
| 2018/0193649 A1* | 7/2018 | Schouenborg ..... A61N 1/36067 |
| 2018/0193655 A1 | 7/2018 | Zhang et al. |
| 2018/0369606 A1 | 12/2018 | Zhang et al. |
| 2018/0369608 A1 | 12/2018 | Chabrol |
| 2019/0001135 A1* | 1/2019 | Yoo .................... A61N 1/36132 |
| 2019/0184174 A1 | 6/2019 | Carcieri et al. |
| 2019/0247664 A1* | 8/2019 | Irazoqui ............. A61N 1/36064 |
| 2019/0282820 A1 | 9/2019 | Bokil |
| 2019/0329049 A1 | 10/2019 | Carcieri et al. |
| 2019/0358458 A1 | 11/2019 | Carcieri et al. |
| 2019/0358461 A1 | 11/2019 | Steinke |
| 2020/0023189 A1* | 1/2020 | Gribetz ............... A61N 1/36196 |
| 2020/0155833 A1 | 5/2020 | Villarta |
| 2020/0155854 A1 | 5/2020 | Leven et al. |
| 2020/0289834 A9 | 9/2020 | Bokil |
| 2020/0376262 A1 | 12/2020 | Clark et al. |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 1997032628 A1 | 9/1997 |
| WO | 1999055411 A3 | 2/2000 |
| WO | 2000038574 A1 | 7/2000 |
| WO | 2001058520 A1 | 8/2001 |
| WO | 2002068042 A1 | 9/2002 |
| WO | 2004045707 A1 | 6/2004 |
| WO | 2008018067 A2 | 2/2008 |
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2009/148939 | 12/2009 |
| WO | 2013162775 A2 | 10/2013 |
| WO | 2014018092 A1 | 1/2014 |

OTHER PUBLICATIONS

Official Communication for U.S. Appl. No. 17/680,020 mailed Jun. 18, 2024.

* cited by examiner

METHODS AND SYSTEMS FOR DEEP BRAIN STIMULATION OF THE NUCLEUS BASALIS OF MEYNERT

CROSS-REFERENCE TO RELATED APPLICATIONS

This application claims the benefit under 35 U.S.C. § 119(e) of U.S. Provisional Patent Application Ser. No. 63/153,775, filed Feb. 25, 2021, which is incorporated herein by reference.

STATEMENT REGARDING FEDERALLY SPONSORED RESEARCH OR DEVELOPMENT

This invention was made with Government support under RF1-AG060754 awarded by the National Institutes of Health. The Government has certain rights in the invention.

FIELD

The present disclosure is directed to the area of methods and systems for deep brain electrical stimulation. The present disclosure is also directed to methods and systems for deep brain stimulation of the nucleus basalis of Meynert (NBM).

BACKGROUND

Implantable electrical stimulation systems have proven therapeutic in a variety of diseases and disorders. For example, deep brain stimulation systems have been used as a therapeutic modality for the treatment of Parkinson's disease, essential tremor, and the like.

Stimulators have been developed to provide therapy for a variety of treatments. A stimulator can include an implantable pulse generator (IPG), one or more leads, and an array of stimulator electrodes on each lead. The stimulator electrodes are in contact with or near the nerves, muscles, or other tissue to be stimulated. The pulse generator in the IPG generates electrical pulses that are delivered by the electrodes to body tissue.

BRIEF SUMMARY

One aspect is a system for stimulation of a nucleus basalis of Meynert (NBM) of a patient. The system includes an implantable electrical stimulation lead including electrodes and configured for implantation of at least one of the electrodes adjacent to or within the NBM of the patient; and an implantable pulse generator coupleable to the implantable electrical stimulation lead and configured for delivering electrical stimulation to the NBM through at least one of the electrodes of the implantable electrical stimulation lead, the implantable pulse generator including at least one processor configured to, upon user request, during an initial stimulation period, which is at least 1 month in duration and has a start and an end, increase over time at least one of a duration or an amplitude of the electrical stimulation from an initial value at the start of the initial stimulation period to a final value at the end of the initial stimulation period.

In at least some aspects, the processor is configured to deliver the electrical stimulation during the initial stimulation period with the increase of the amplitude of the electrical stimulation over time. In at least some aspects, the processor is configured to deliver the electrical stimulation during the initial stimulation period with the increase of the duration of the electrical stimulation over time. In at least some aspects, the processor is configured to deliver the electrical stimulation during the initial stimulation period with the increase of the amplitude of the electrical stimulation over time.

In at least some aspects, the increase over time of the at least one of the duration or the amplitude includes increasing the at least one of the duration or the amplitude from the initial value to the final value according to a linear ramp. In at least some aspects, the increase over time of at least one of the duration or the amplitude includes increasing the at least one of the duration or the amplitude from the initial value to the final value according to a non-linear ramp.

In at least some aspects, the processor is further configured, during the initial stimulation period, to not deliver the electrical stimulation during periods in which a cognitive load is expected for the patient. In at least some aspects, the processor is further configured to indicate to a user at least one of i) electrical stimulation is being delivered or ii) electrical stimulation is soon to be delivered, wherein the processor is further configured to provide a control for the user to postpone the delivery of the electrical stimulation and, upon actuation of the control, to postpone the delivery of the electrical stimulation.

In at least some aspects, the system further includes a sensor selected from a blood flow sensor, an electroencephalography (EEG) sensor, an electrocorticography (ECoG) sensor, a movement sensor, a chemical concentration sensor, an enzyme activity sensor, or any combination thereof, wherein the sensor is configured for monitoring response of the patient to the electrical stimulation. In at least some aspects, the processor is configured to monitor alpha wave brain activity of the patient using the EEG or ECoG sensor.

Another aspect is a method for stimulating a nucleus basalis of Meynert (NBM) of a patient. The method includes implanting an electrical stimulation lead in a brain of the patient, wherein the electrical stimulation lead includes electrodes and at least one of the electrodes is disposed adjacent to or within the NBM of the patient; and delivering electrical stimulation to the NBM through at least one of the electrodes, wherein during an initial stimulation period, which is at least 1 month in duration and has a start and an end, at least one of a duration or an amplitude of the electrical stimulation increases over time from an initial value at the start of the initial stimulation period to a final value at the end of the initial stimulation period.

A further aspect is a method for stimulating a nucleus basalis of Meynert (NBM) of a patient. The method includes implanting an electrical stimulation lead in a lateral-to-medial trajectory into a brain of the patient, wherein the electrical stimulation lead includes electrodes and at least one of the electrodes is disposed adjacent to or within the NBM of the patient; and delivering electrical stimulation to the NBM through at least one of the electrodes, wherein during an initial stimulation period, which is at least 1 month in duration, the electrical stimulation is not delivered during periods in which a cognitive load for the patient is expected.

In at least some aspects, the method further includes, prior to, or during, delivery of the electrical stimulation, indicating to a user that the electrical stimulation is being delivered or soon to be delivered. In at least some aspects, the method further includes, in response to user operation of a postponement control, postponing the delivery of the electrical stimulation. In at least some aspects, the method further includes, after the initial stimulation period, increasing, over time, an amount of daily time during which the electrical stimulation is delivered during the periods in which the cognitive load for the patient is expected.

In at least some aspects, the method further includes, during the initial stimulation period, increasing over time at least one of a duration or an amplitude of the electrical stimulation from an initial value at a start of the initial stimulation period to a final value at an end of the initial stimulation period. In at least some aspects, the increasing includes increasing over time the at least one of the duration or the amplitude from the initial value to the final value according to a linear ramp. In at least some aspects, the increasing includes increasing over time the at least one of the duration or the amplitude from the initial value to the final value according to a non-linear ramp.

In at least some aspects, the method further includes monitoring the patient using a sensor selected from a blood flow sensor, an electroencephalography (EEG) sensor, an electrocorticography (ECoG) sensor, a movement sensor, or any combination thereof.

Yet another aspect is a system for stimulation of a nucleus basalis of Meynert (NBM) of a patient. The system includes an implantable electrical stimulation lead including electrodes and configured for implantation of at least one of the electrodes adjacent to or within the NBM of the patient; and an implantable pulse generator coupleable to the implantable electrical stimulation lead and configured for delivering electrical stimulation to the NBM through at least one of the electrodes of the implantable electrical stimulation lead, the implantable pulse generator including at least one processor configured to, upon user request, during an initial stimulation period, which is at least 1 month in duration and has a start and an end, not deliver the electrical stimulation during periods in which a cognitive load for the patient is expected.

Another aspect is a method for stimulating a nucleus basalis of Meynert (NBM) of a patient. The method includes implanting an electrical stimulation lead in a brain of the patient, wherein the electrical stimulation lead includes electrodes and at least one of the electrodes is disposed adjacent to or within the NBM of the patient; delivering electrical stimulation to the NBM through at least one of the electrodes; monitoring the patient using a sensor selected from a blood flow sensor, an electroencephalography (EEG) sensor, an electrocorticography (ECoG) sensor, a movement sensor, or any combination thereof; and modifying the electrical stimulation based on the monitoring of the sensor.

In at least some aspects, monitoring the patient includes monitoring alpha wave brain activity of the patient using the EEG or ECoG sensor.

A further aspect is a system for stimulation of a nucleus basalis of Meynert (NBM) of a patient. The system includes an implantable electrical stimulation lead including a plurality of electrodes and configured for implantation of at least one of the electrodes adjacent to or within the NBM of the patient; and an implantable pulse generator coupleable to the implantable electrical stimulation lead and configured for delivering electrical stimulation to the NBM through at least one of the electrodes of the implantable electrical stimulation lead. The implantable pulse generator includes at least one processor configured to deliver electrical stimulation to the NBM through at least one of the electrodes; monitor the patient using a sensor selected from a blood flow sensor, an electroencephalography (EEG) sensor, an electrocorticography (ECoG) sensor, a movement sensor, or any combination thereof; and modify the electrical stimulation based on the monitoring of the sensor.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present disclosure is directed to the area of methods and systems for deep brain electrical stimulation. The present disclosure is also directed to methods and systems for deep brain stimulation of the nucleus basalis of Meynert (NBM).

Suitable implantable electrical stimulation systems include, but are not limited to, a least one electrical stimulation lead with one or more electrodes disposed along a distal end of the lead and one or more terminals disposed along the one or more proximal ends of the lead. Examples of electrical stimulation systems with leads are found in, for example, U.S. Pat. Nos. 6,181,969; 6,295,944; 6,391,985; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,831,742; 8,688,235; 8,175,710; 8,224,450; 8,271,094; 8,295,944; 8,364,278; and 8,391,985; U.S. Patent Application Publications Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated by reference in their entireties.

Figure 1:
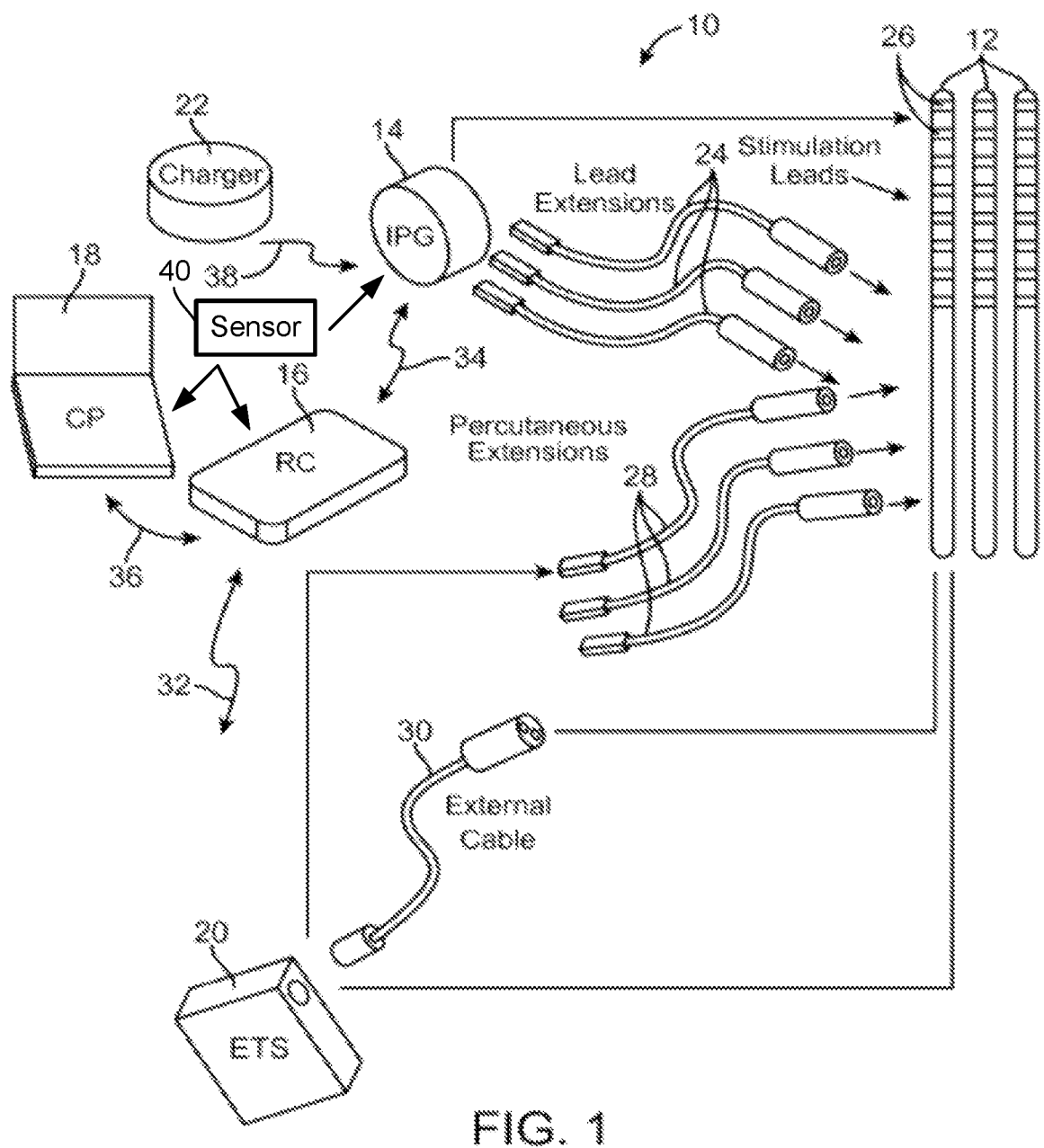
FIG. 1 is a schematic view of one embodiment of an electrical stimulation system that includes one or more leads that can be coupled to an IPG.

Turning to FIG. 1, one embodiment of an electrical stimulation system 10 includes one or more electrical stimulation leads 12 and an implantable pulse generator (IPG) 14. The system 10 can also include one or more of an external remote control (RC) 16, a clinician's programmer (CP) 18, an external trial stimulator (ETS) 20, or an external charger 22. The IPG and ETS are examples of control modules for the electrical stimulation system.

The IPG 14 is physically connected, optionally via one or more lead extensions 24, to the electrical stimulation lead(s) 12. Each electrical stimulation lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to one or more electrodes 26 of the array in accordance with a set of stimulation parameters. The IPG 14 can be implanted into a patient's body, for example, below the patient's clavicle area or within the patient's abdominal cavity or at any other suitable site. The implantable pulse generator 14 can have multiple stimulation channels which may be independently programmable to control the magnitude of the current stimulus from each channel. In some embodiments, the implantable pulse generator 14 can have any suitable number of stimulation channels including, but not limited to, 4, 6, 8, 12, 16, 32, or more stimulation channels. The implantable pulse generator 14 can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrodes 26 in accordance with a set of stimulation parameters. One difference between the ETS 20 and the IPG 14 is that the ETS 20 is often a non-implantable device that is used on a trial basis after the electrical stimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and electrical stimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions. Alternately, or additionally, stimulation parameters can be programed via wireless communications (e.g., Bluetooth) between the RC 16 (or external device such as a hand-held electronic device like a mobile phone, tablet, or the like) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

Additional examples of the RC 16, CP 18, ETS 20, and external charger 22 can be found in the references cited herein as well as U.S. Pat. Nos. 6,895,280; 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, all of which are incorporated herein by reference in their entireties.

Figure 2:
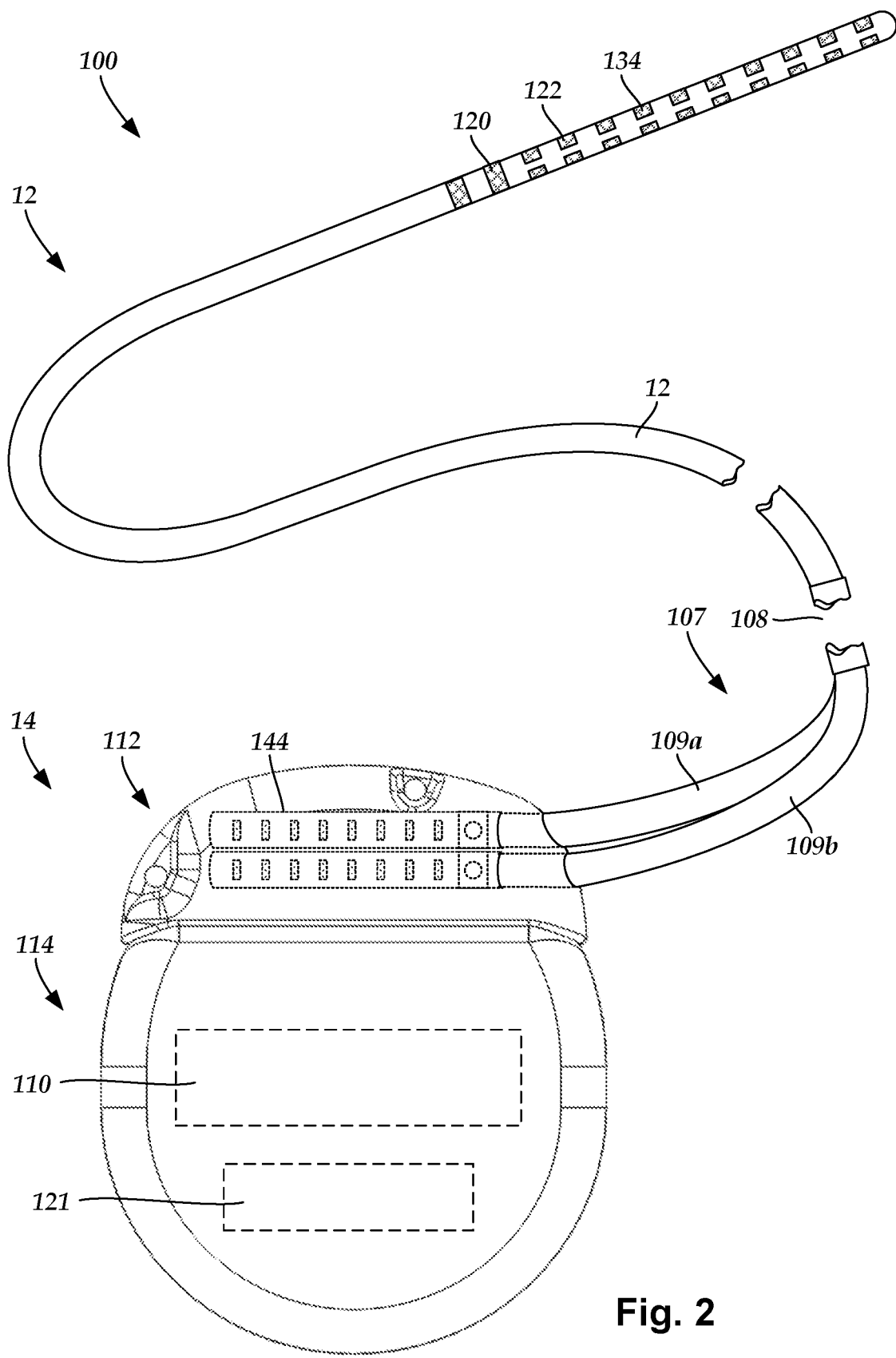
FIG. 2 is a schematic view of another embodiment of an electrical stimulation system that includes a percutaneous lead coupled to an IPG.

FIG. 2 illustrates schematically another embodiment of an electrical stimulation system 10. The electrical stimulation system includes an IPG (e.g., a control module) 14 and at least one electrical stimulation lead 12 coupleable to the IPG 14. The electrical stimulation lead 12 includes one or more lead bodies 106, an array of electrodes, such as electrode 134, and an array of terminals (e.g., 210 in FIGS. 3 and 4) disposed along the one or more lead bodies 106. In at least some embodiments, the lead is isodiametric along a longitudinal length of the lead body 106. FIG. 2 illustrates one lead 12 coupled to an IPG 14. Other embodiments may include two, three, four, or more leads 12 coupled to the IPG 14.

The electrical stimulation lead 12 can be coupled to the IPG 14 in any suitable manner. In at least some embodiments, the electrical stimulation lead 12 couples directly to the IPG 14. In at least some other embodiments, the electrical stimulation lead 12 couples to the IPG 14 via one or more intermediate devices. For example, in at least some embodiments one or more lead extensions 224 (see e.g., FIG. 4) can be disposed between the electrical stimulation lead 12 and the IPG 14 to extend the distance between the electrical stimulation lead 12 and the IPG 14. Lead extensions may also be useful to cross a joint or can be more easily replaced if the lead extension breaks due to fatigue as such replacement will not affect the placement of the distal end of the lead. Other intermediate devices may be used in addition to, or in lieu of, one or more lead extensions including, for example, a splitter, an adaptor, or the like or any combination thereof. It will be understood that, in the case where the electrical stimulation system 10 includes multiple elongated devices disposed between the electrical stimulation lead 12 and the IPG 14, the intermediate devices may be configured into any suitable arrangement.

In FIG. 2, the electrical stimulation system 10 is shown having a splitter 107 configured and arranged for facilitating coupling of the electrical stimulation lead 12 to the IPG 14. The splitter 107 includes a splitter connector 108 configured to couple to a proximal end of the electrical stimulation lead 12, and one or more splitter tails 109a and 109b configured and arranged to couple to the IPG 14 (or another splitter, a lead extension, an adaptor, or the like).

In at least some embodiments, the IPG 14 includes a connector housing 112 and a sealed electronics housing 114. An electronic subassembly 110 and an optional power source 121 are disposed in the electronics housing 114. An IPG connector 144 is disposed in the connector housing 112. The IPG connector 144 is configured and arranged to make an electrical connection between the electrical stimulation lead 12 and the electronic subassembly 110 of the IPG 14.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. Any number of electrodes 134 can be used for each array 26. For example, there can be two, four, six, eight, ten, twelve, fourteen, sixteen, or more electrodes 134. As will be recognized, other numbers of electrodes 134 may also be used.

The electrodes of the one or more lead bodies 106 are typically disposed in, or separated by, a non-conductive, biocompatible material such as, for example, silicone, polyurethane, polyetheretherketone ("PEEK"), epoxy, and the like or combinations thereof. The lead bodies 106 may be formed in the desired shape by any process including, for example, molding (including injection molding), casting, and the like. The non-conductive material typically extends from the distal end of the one or more lead bodies 106 to the proximal end of each of the one or more lead bodies 106.

Figure 3:
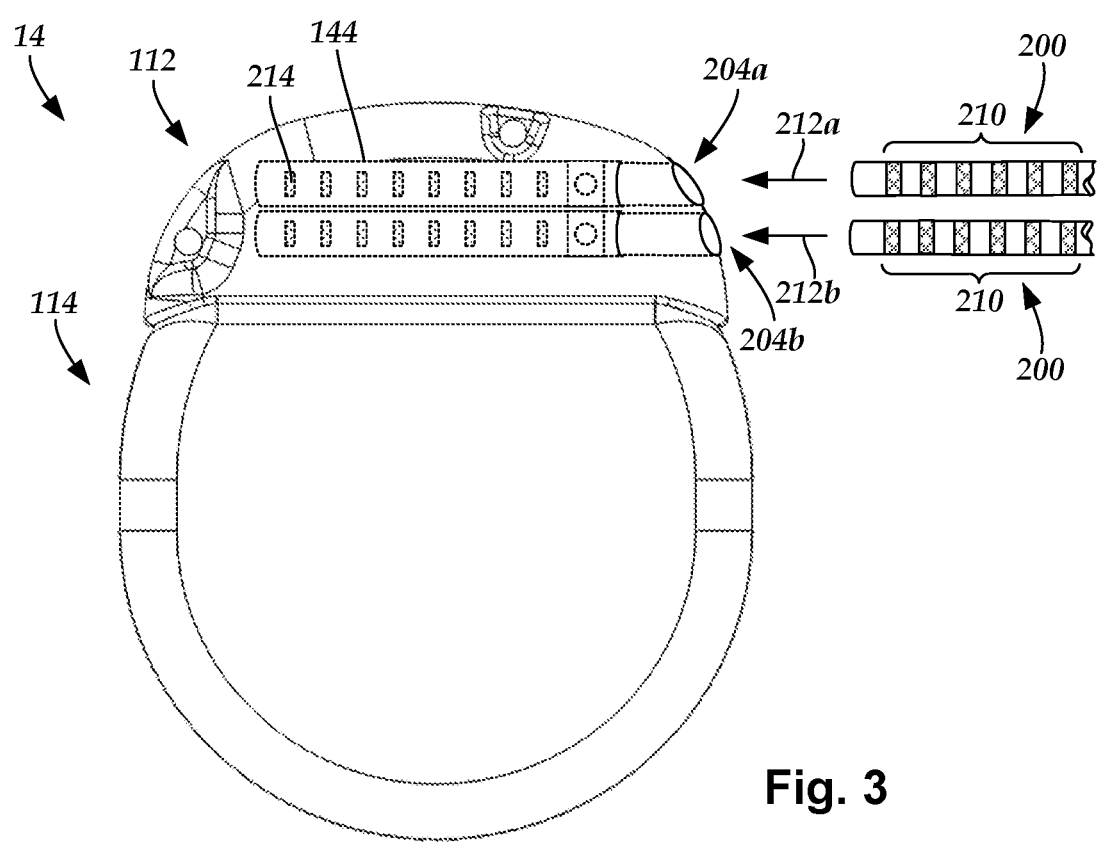
FIG. 3 is a schematic view of one embodiment of a plurality of connector assemblies disposed in the IPG of FIG. 2, the connector assemblies configured and arranged to receive the proximal portions of the leads of FIG. 2.
Figure 4:
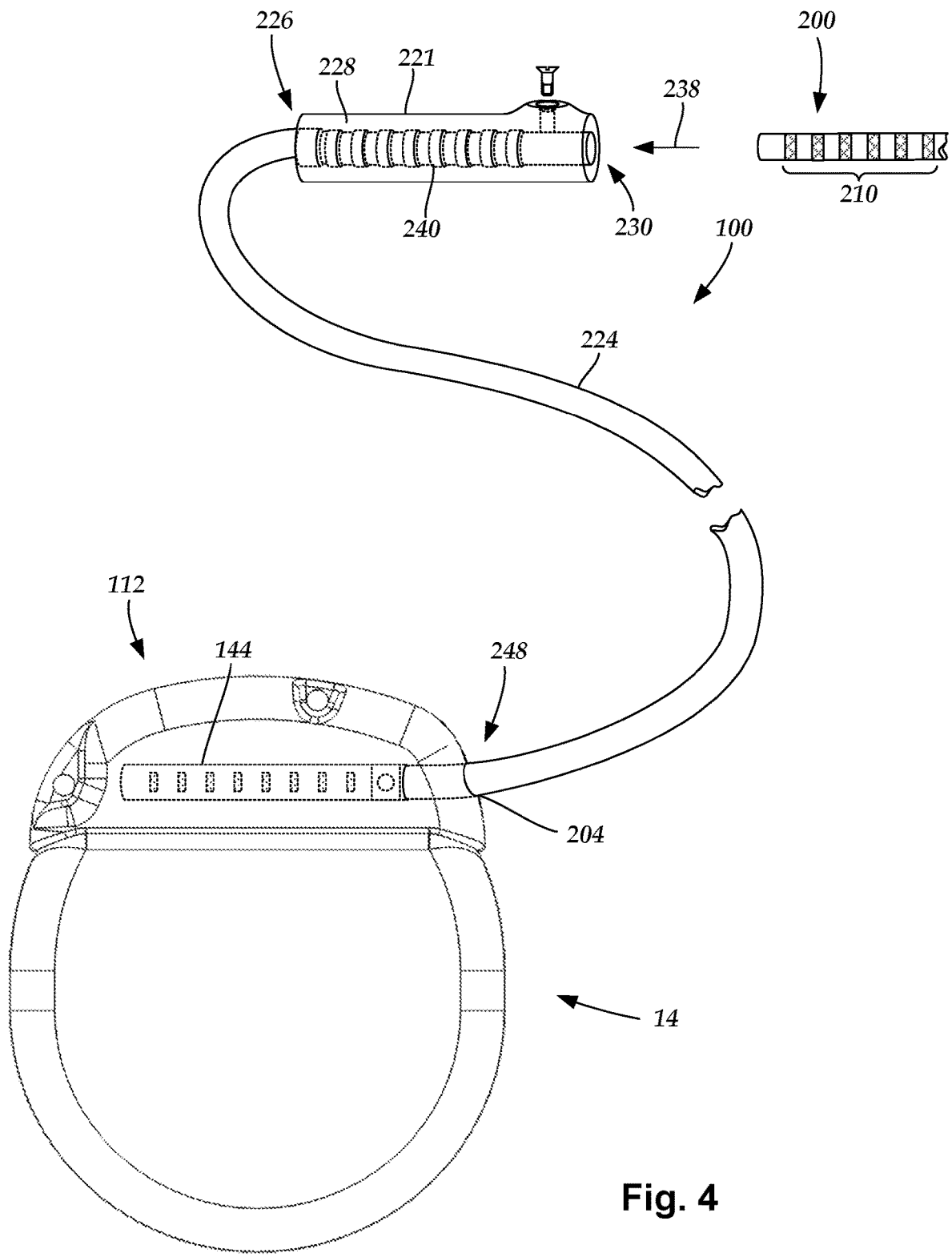
FIG. 4 is a schematic view of one embodiment of a proximal portion of the lead of FIG. 2, a lead extension, and the IPG of FIG. 2, the lead extension configured and arranged to couple the lead to the IPG.

Terminals (e.g., 210 in FIGS. 3 and 4) are typically disposed along the proximal end of the one or more lead bodies 106 of the electrical stimulation system 10 (as well as any splitters, lead extensions, adaptors, or the like) for electrical connection to corresponding connector contacts (e.g., 214 in FIGS. 3 and 240 in FIG. 4). The connector contacts are disposed in connectors (e.g., 144 in FIGS. 2 to 4; and 221 in FIG. 4) which, in turn, are disposed on, for example, the IPG 14 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the lead body 106, for example, for inserting a stylet to facilitate placement of the lead body 106 within a body of a patient. Additionally, there may be one or more lumens (not shown) that open at, or near, the distal end of the lead body 106, for example, for infusion of drugs or medication into the site of implantation of the one or more lead bodies 106. In at least some embodiments, the one or more lumens are permanently or removably sealable at the distal end.

FIG. 3 is a schematic side view of one embodiment of a proximal end of one or more elongated devices 200 configured and arranged for coupling to one embodiment of the IPG connector 144. The one or more elongated devices may include, for example, the lead body 106, one or more intermediate devices (e.g., the splitter 107 of FIG. 2, the lead extension 224 of FIG. 4, an adaptor, or the like or combinations thereof), or a combination thereof. FIG. 3 illustrates two elongated devices 200 coupled to the IPG 14. These two elongated devices 200 can be two tails as illustrated in FIG. 2 or two different leads or any other combination of elongated devices.

The IPG connector 144 defines at least one port into which a proximal end of the elongated device 200 can be inserted, as shown by directional arrows 212a and 212b. In FIG. 3 (and in other figures), the connector housing 112 is shown having two ports 204a and 204b. The connector housing 112 can define any suitable number of ports including, for example, one, two, three, four, five, six, seven, eight, or more ports.

The IPG connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the IPG 14 to the electrodes (134 of FIG. 2) disposed at a distal end of the electrical stimulation lead 12. Examples of connectors in IPGs are found in, for example, U.S. Pat. Nos. 7,244,150 and 8,224,450, which are incorporated by reference in their entireties.

FIG. 4 is a schematic side view of another embodiment of the electrical stimulation system 10. The electrical stimulation system 10 includes a lead extension 224 that is configured and arranged to couple one or more elongated devices 200 (e.g., the lead body 106, the splitter 107, an adaptor, another lead extension, or the like or combinations thereof) to the IPG 14. In FIG. 4, the lead extension 224 is shown coupled to a single port 204 defined in the IPG connector 144. Additionally, the lead extension 224 is shown configured and arranged to couple to a single elongated device 200. In alternate embodiments, the lead extension 224 is configured and arranged to couple to multiple ports 204 defined in the IPG connector 144, or to receive multiple elongated devices 200, or both.

A lead extension connector 221 is disposed on the lead extension 224. In FIG. 4, the lead extension connector 221 is shown disposed at a distal end 226 of the lead extension 224. The lead extension connector 221 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 2) disposed along the lead (12 in FIG. 2).

In at least some embodiments, the proximal end of the lead extension 224 is similarly configured and arranged as a proximal end of the lead 12 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 4), the proximal end 248 of the lead extension 224 is configured and arranged for insertion into the IPG connector 144.

Returning to FIG. 2, in at least some embodiments at least some of the stimulation electrodes take the form of segmented electrodes that extend only partially around the perimeter (for example, the circumference) of the lead. These segmented electrodes can be provided in sets of electrodes, with each set having electrodes circumferentially distributed about the lead at a particular longitudinal position.

In FIG. 2, the electrodes 134 are shown as including both ring electrodes 120 and segmented electrodes 122. In some embodiments, the electrodes 134 are all segmented electrode or all ring electrodes. The segmented electrodes 122 of FIG. 2 are in sets of three (one of which is not visible in FIG. 2), where the three segmented electrodes of a particular set are electrically isolated from one another and are circumferentially offset along the lead 12. Any suitable number of segmented electrodes can be formed into a set including, for example, two, three, four, or more segmented electrodes. The lead 12 of FIG. 2 has thirty segmented electrodes 122 (ten sets of three electrodes each) and two ring electrodes 120 for a total of 32 electrodes 134.

Segmented electrodes can be used to direct stimulus current to one side, or even a portion of one side, of the lead. When segmented electrodes are used in conjunction with an implantable pulse generator that delivers multiple current stimuli simultaneously, current steering can be achieved to deliver the stimulus more precisely to a position around an axis of the lead (i.e., radial positioning around the axis of the lead). Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a segmented electrode array, current steering can be performed not only along a length of the lead but also around a perimeter of the lead. This provides precise three-dimensional targeting and delivery of the current stimulus to neural target tissue, while potentially avoiding stimulation of other tissue.

Figure 5A:
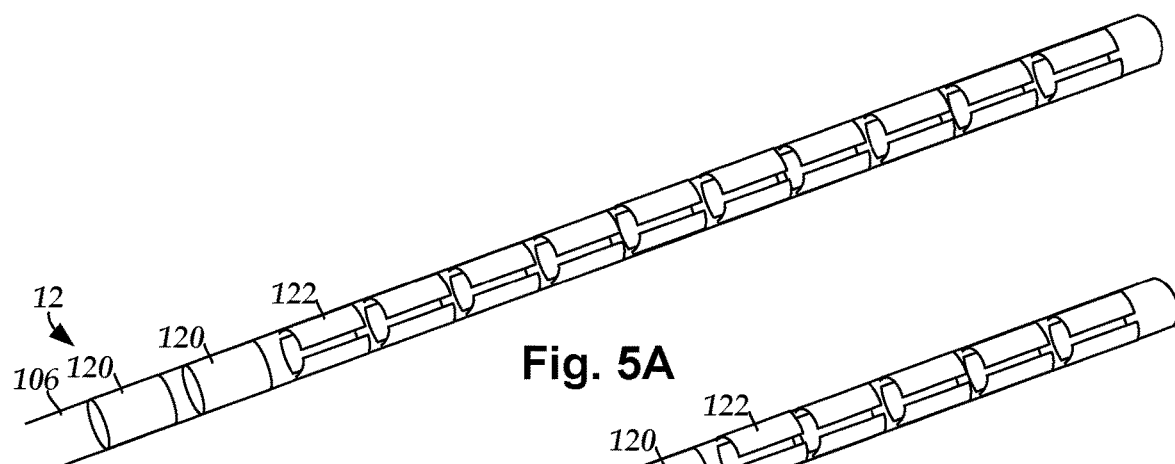
FIG. 5A is a schematic perspective view of a portion of one embodiment of a lead with thirty-two electrodes.

FIG. 5A illustrates a 32-electrode lead 12 with a lead body 106 and two ring electrodes 120 proximal to thirty segmented electrodes 122 arranged in ten sets of three segmented electrodes each. In the illustrated embodiments, the ring electrodes 120 are proximal to the segmented electrodes 122. In other embodiments, one or more of the ring electrodes 120 can be proximal to, or distal to, one or more of the segmented electrodes 122.

Any number of segmented electrodes 122 may be disposed on the lead body including, for example, one, two, three, four, five, six, seven, eight, nine, ten, eleven, twelve, thirteen, fourteen, fifteen, sixteen, twenty, twenty-four, twenty-eight, thirty, thirty-two, or more segmented electrodes 122. It will be understood that any number of segmented electrodes 122 may be disposed along the length of the lead body. A segmented electrode 122 typically extends only 75%, 67%, 60%, 50%, 40%, 33%, 25%, 20%, 17%, 15%, or less around the circumference of the lead.

The segmented electrodes 122 may be grouped into sets of segmented electrodes, where each set is disposed around a circumference of the electrical stimulation lead 12 at a particular longitudinal portion of the electrical stimulation lead 12. The electrical stimulation lead 12 may have any number of segmented electrodes 122 in a given set of segmented electrodes. The electrical stimulation lead 12 may have one, two, three, four, five, six, seven, eight, or more segmented electrodes 122 in a given set. The electrical stimulation lead 12 may have any number of sets of segmented electrodes including, but not limited to, one, two, three, four, five, six, eight, ten, twelve, fifteen, sixteen, twenty, or more sets. The segmented electrodes 122 may be uniform, or vary, in size and shape. In some embodiments, the segmented electrodes 122 are all of the same size, shape, diameter, width or area or any combination thereof. In some embodiments, the segmented electrodes 122 of each circumferential set (or even all segmented electrodes disposed on the lead 12) may be identical in size and shape.

Each set of segmented electrodes 122 may be disposed around the circumference of the lead body to form a substantially cylindrical shape around the lead body. The spacing between individual electrodes of a given set of the segmented electrodes may be the same, or different from, the spacing between individual electrodes of another set of segmented electrodes on the electrical stimulation lead 12. In at least some embodiments, equal spaces, gaps, or cutouts are disposed between each segmented electrode 122 around the circumference of the lead body. In other embodiments, the spaces, gaps, or cutouts between the segmented electrodes 122 may differ in size or shape. In other embodiments, the spaces, gaps, or cutouts between segmented electrodes 122 may be uniform for a particular set of the segmented electrodes 122, or for all sets of the segmented electrodes 122. The sets of segmented electrodes 122 may be positioned in irregular or regular intervals along a length of the lead body.

Figure 5B:
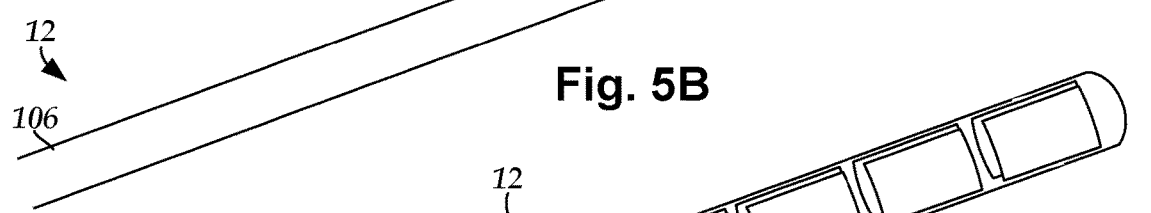
FIG. 5B is a schematic perspective view of portions of one embodiment of a lead with sixteen electrodes.
Figure 5C:
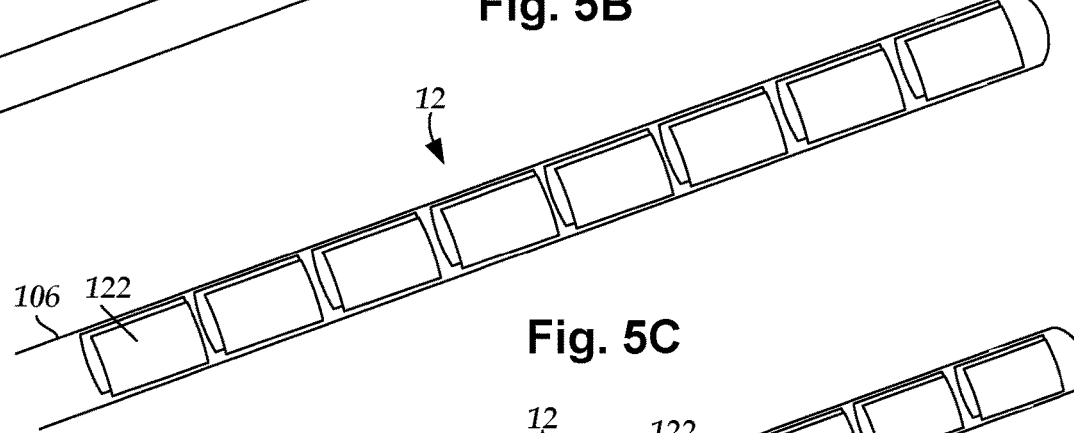
FIG. 5C is a schematic perspective view of portions of another embodiment of a lead with sixteen electrodes.
Figure 5D:
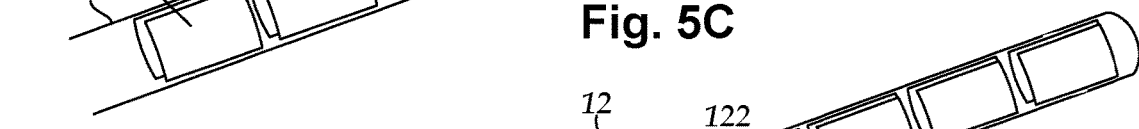
FIG. 5D is a schematic perspective view of portions of a third embodiment of a lead with sixteen electrodes.
Figure 5E:
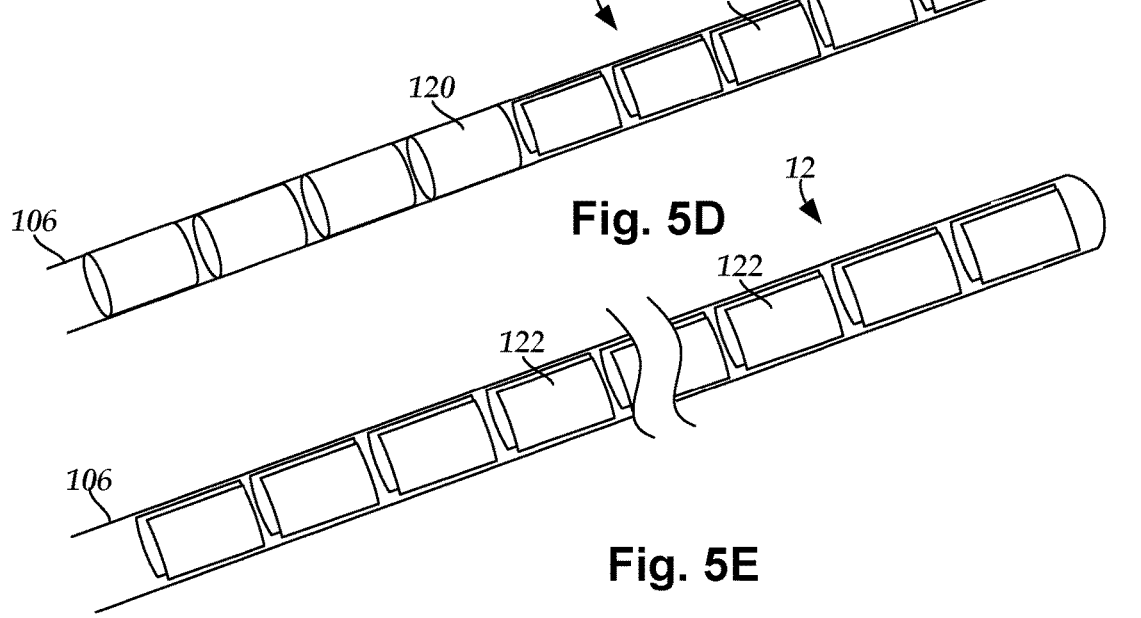
FIG. 5E is a schematic perspective view of a portion of another embodiment of a lead with thirty-two electrodes.

FIG. 5B to 5E illustrate other embodiments of leads with segmented electrodes 122. FIG. 5B illustrates a sixteen electrode lead 12 having one ring electrode 120 that is proximal to five sets of three segmented electrodes 122 each. FIG. 5C illustrates a sixteen electrode lead 12 having eight sets of two segmented electrodes 122 each. As illustrated in FIG. 5C, an embodiment of a lead 12 does not necessarily include a ring electrode. FIG. 5D illustrates a sixteen electrode lead 12 having four ring electrodes 120 that are proximal to six sets of two segmented electrodes 122 each. FIG. 5E illustrates a thirty-two electrode lead 12 having sixteen sets of two segmented electrodes 122 each (for clarity of illustration, not all of the electrodes are shown). It will be recognized that any other electrode combination of ring electrodes, segmented electrodes, or both types of electrodes can be used.

When the lead 12 includes both ring electrodes 120 and segmented electrodes 122, the ring electrodes 120 and the segmented electrodes 122 may be arranged in any suitable configuration. For example, when the lead 12 includes two or more ring electrodes 120 and one or more sets of segmented electrodes 122, the ring electrodes 120 can flank the one or more sets of segmented electrodes 122. Alternately, the two or more ring electrodes 120 can be disposed proximal to the one or more sets of segmented electrodes 122 or the two or more ring electrodes 120 can be disposed distal to the one or more sets of segmented electrodes 122 or any other suitable arrangement of the ring electrodes 120 and segmented electrodes 122.

The electrodes 120, 122 may have any suitable longitudinal length including, but not limited to, 1, 1.5, 2, 3, 4, 4.5, 5, or 6 mm. The longitudinal spacing between adjacent electrodes 120, 122 may be any suitable amount including, but not limited to, 0.25, 0.5, 0.75, 1, 2, or 3 mm, where the spacing is defined as the distance between the nearest edges of two adjacent electrodes. In some embodiments, the spacing is uniform between longitudinally adjacent of electrodes along the length of the lead. In other embodiments, the spacing between longitudinally adjacent electrodes may be different or non-uniform along the length of the lead.

Examples of electrical stimulation leads with segmented electrodes include U.S. Patent Application Publications Nos. 2010/0268298; 2011/0005069; 2011/0078900; 2011/0130803; 2011/0130816; 2011/0130817; 2011/0130818; 2011/0078900; 2011/0238129; 2011/0313500; 2012/0016378; 2012/0046710; 2012/0071949; 2012/0165911; 2012/0197375; 2012/0203316; 2012/0203320; 2012/0203321; 2013/0197602; 2013/0261684; 2013/0325091; 2013/0317587; 2014/0039587; 2014/0353001; 2014/0358209; 2014/0358210; 2015/0018915; 2015/0021817; 2015/0045864; 2015/0021817; 2015/0066120; 2013/0197424; 2015/0151113; 2014/0358207; and U.S. Pat. No. 8,483,237, all of which are incorporated herein by reference in their entireties. An electrical stimulation lead may also include a tip electrode and examples of leads with tip electrodes include at least some of the previously cited references, as well as U.S. Patent Application Publications Nos. 2014/0296953 and 2014/0343647, all of which are incorporated herein by reference in their entireties. A lead with segmented electrodes may be a directional lead that can provide stimulation in a particular direction using the segmented electrodes.

Figure 6:
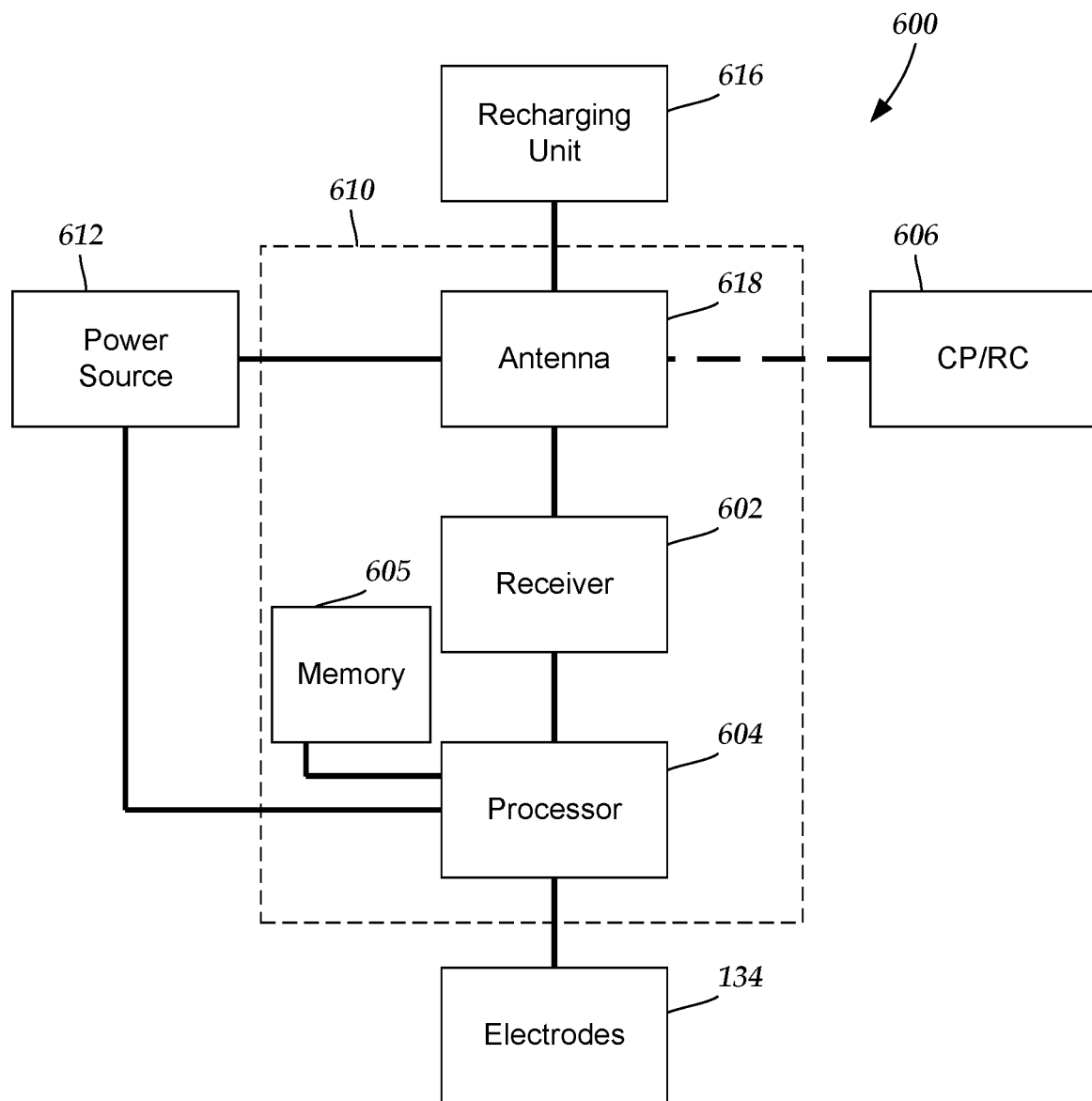
FIG. 6 is a schematic overview of one embodiment of components of an electrical stimulation system.

FIG. 6 is a schematic overview of one embodiment of components of an electrical stimulation system 600 including an electronic subassembly 610 disposed within an IPG. It will be understood that the electrical stimulation system can include more, fewer, or different components and can have a variety of different configurations including those configurations disclosed in the stimulator references cited herein.

Some of the components (for example, power source 612, antenna 618, receiver 602, processor 604, and memory 605) of the electrical stimulation system can be positioned on one or more circuit boards or similar carriers within a sealed housing of an implantable pulse generator, if desired. Any power source 612 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference in its entirety.

As another alternative, power can be supplied by an external power source through inductive coupling via the optional antenna 618 or a secondary antenna. The external power source can be in a device that is mounted on the skin of the user or in a unit that is provided near the user on a permanent or periodic basis.

If the power source 612 is a rechargeable battery, the battery may be recharged using the optional antenna 618, if desired. Power can be provided to the battery for recharging by inductively coupling the battery through the antenna to a recharging unit 616 external to the user. Examples of such arrangements can be found in the references identified above.

In one embodiment, electrical current is emitted by the electrodes 134 on the lead body to stimulate nerve fibers, muscle fibers, or other body tissues near the electrical stimulation system. A processor 604 is generally included to control the timing and electrical characteristics of the electrical stimulation system. For example, the processor 604 can, if desired, control one or more of the timing, frequency, amplitude, width, and waveform of the pulses. In addition, the processor 604 can select which electrodes can be used to provide stimulation, if desired. In some embodiments, the processor 604 may select which electrode(s) are cathodes and which electrode(s) are anodes and the amount of anodic or cathodic current assigned to each. In some embodiments, the processor 604 may be used to identify which electrodes provide the most useful stimulation of the desired tissue. Instructions for the processor 604 can be stored on the memory 605.

Any processor can be used and can be as simple as an electronic device that, for example, produces pulses at a regular interval or the processor can be capable of receiving and interpreting instructions from the CP/RC 606 (such as CP 18 or RC 16 of FIG. 1) that, for example, allows modification of pulse characteristics. In the illustrated embodiment, the processor 604 is coupled to a receiver 602 which, in turn, is coupled to the optional antenna 618. This allows the processor 604 to receive instructions from an external source to, for example, direct the pulse characteristics and the selection of electrodes, if desired.

In one embodiment, the antenna 618 is capable of receiving signals (e.g., RF signals) from a CP/RC 606 (see, CP 18 or RC 16 of FIG. 1) which is programmed or otherwise operated by a user. The signals sent to the processor 604 via the antenna 618 and receiver 602 can be used to modify or otherwise direct the operation of the electrical stimulation system. For example, the signals may be used to modify the pulses of the electrical stimulation system such as modifying one or more of pulse width, pulse frequency, pulse waveform, and pulse amplitude. The signals may also direct the electrical stimulation system 600 to cease operation, to start operation, to start charging the battery, or to stop charging the battery. In other embodiments, the stimulation system does not include an antenna 618 or receiver 602 and the processor 604 operates as programmed.

Optionally, the electrical stimulation system 600 may include a transmitter (not shown) coupled to the processor 604 and the antenna 618 for transmitting signals back to the CP/RC 606 or another unit capable of receiving the signals. For example, the electrical stimulation system 600 may transmit signals indicating whether the electrical stimulation system 600 is operating properly or not or indicating when the battery needs to be charged or the level of charge remaining in the battery. The processor 604 may also be capable of transmitting information about the pulse characteristics so that a user or clinician can determine or verify the characteristics.

Dementias like Alzheimer's disease are generally associated with the reduction of a key neurotransmitter, Acetylcholine (Ach), in the cortex. Studies suggest that anticholinergic medications (for other health issues) are associated with an increased likelihood of dementia, and one of the FDA approved classes of drugs for dementia is an anticholinesterase (i.e., a drug to slow metabolism of ACh so that it can have a longer/stronger effect).

The cells that produce ACh and send and release it in the cortex are located in the nucleus basalis of Meynert (NBM). It is thought that stimulation of this region can evoke a release of ACh in the cortex and counteract effects of dementia. The release of ACh may also be used to treat depression and neuropsychological disorders. It has been demonstrated that in non-human primates stimulation of the NBM notably improves performance in a memory task. It has also been shown that an intermittent stimulation protocol is effective, but that a continuous stimulation protocol is not effective, perhaps because synaptic machinery is overworked.

In addition to stimulating the NBM neurons to deliver more ACh, it is desirable to also slow or halt the neurodegeneration of those cells.

Figure 7:
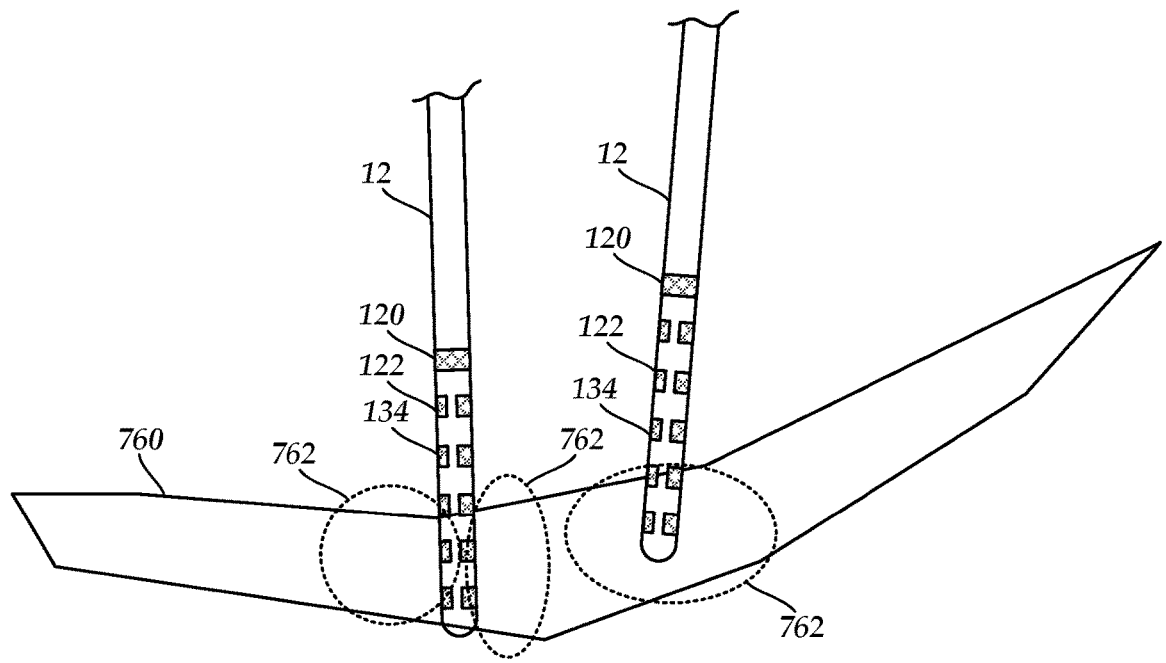
FIG. 7 is schematic side view of one embodiment of a method of stimulating the nucleus basalis of Meynert (NBM) using two electrical stimulation leads.

The NBM has a unique, curved shape that may be characterized as a bent oval pancake or a flat banana. An approximation of the shape of the NBM 760 of one hemisphere of the brain is illustrated in FIG. 7. The shape can make the NBM 760 difficult to fully engage using an electrical stimulation lead as it may be difficult for one electrode array to stimulate a relatively large portion, or even all, of the cells to take full advantage of the ACh machinery of each cell.

In at least some embodiments, to address the unique shape of the target NBM 760 and to stimulate more of the target NBM, multiple electrical stimulation leads 12 can be placed at different parts of the target NBM 760, and stimulation can be cycled between the electrodes 134 of the electrical stimulation leads 12 to produce multiple stimulation regions 762, as illustrated in FIG. 7. In the illustrated embodiment of FIG. 7, two electrical stimulation leads 12 are implanted using a superior-to-inferior trajectory and one electrical stimulation lead is used to produce two different stimulation regions 762 and the other electrical stimulation lead provides another stimulation region.

Figure 8:
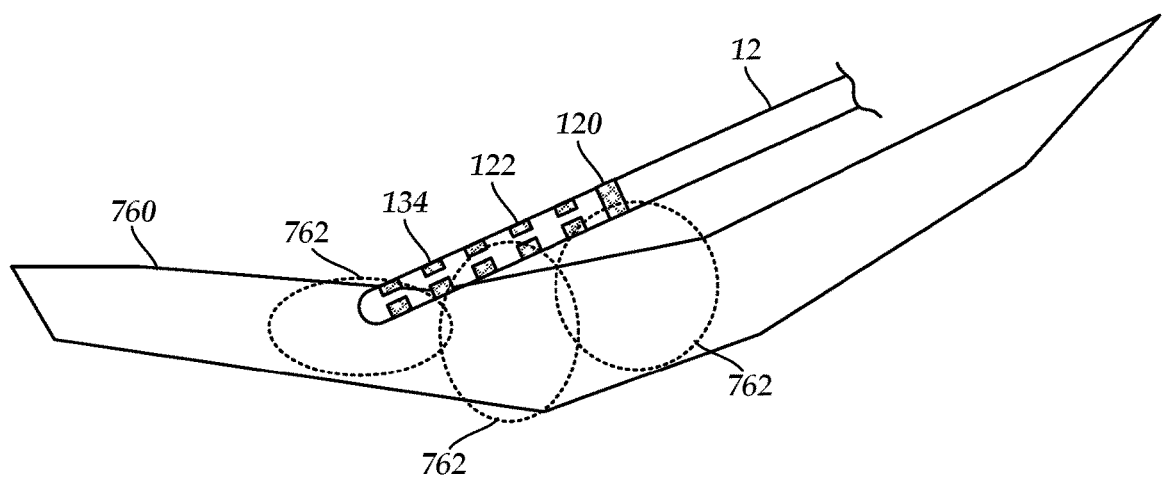
FIG. 8 is schematic side view of one embodiment of a method of stimulating the NBM using one electrical stimulation lead implanted in a lateral-to-medial trajectory.

In at least some embodiments, as illustrated in FIG. 8, to address the unique shape of the target NBM 760, to stimulate more of the target, at least one stimulation lead 12 can be implanted along a lead trajectory that is generally or approximately (for example, within 10, 15, 25, 30, or 45 degrees) oriented lateral-to-medial, rather than the typical superior-to-inferior, to align electrodes 134 of the lead along or adjacent the axis of the target NBM 760. Along this lead trajectory, more electrodes 134 from a single electrical stimulation lead 12 can be near (including traversing) portions of the target NBM 760 to produce multiple stimulation regions 762 which can be cycled through as described in more detail below.

Any suitable number of electrical stimulation leads 12 can be used to stimulate the NBM including, but not limited to, one, two, three, four, or more leads. When multiple electrical stimulation leads 12 are used, there can be any suitable combination of electrical stimulation lead(s) 12 implanted in the superior-to-inferior trajectory (FIG. 7) and lead(s) implanted in the lateral-to-medial trajectory (FIG. 8). Electrical stimulation lead(s) 12 can be implanted in one or both hemispheres of the brain to stimulate one or both NBMs 760. The arrangement of electrical stimulation lead(s) 12 for each hemisphere can be the same or different.

An electrical stimulation lead 12 can produce any suitable number of stimulation regions 762 including, but not limited to, one, two, three, four, or more stimulation regions. In at least some embodiments, one or more electrical stimulation leads 12 include segmented electrodes 122. The use of segmented electrodes 122 may facilitate the selection of directionality of the stimulation regions 762.

One or more electrodes 134 can be used to generate the electrical stimulation for a stimulation region 762. The electrode(s) can be cathodes or anodes or any combination thereof. In at least some embodiments, the sealed electronics housing 114 (or other portion of the case) of the IPG 14 can be used as a return electrode, which is often the case for monopolar electrical stimulation. Multipolar electrical stimulation can also be used. In at least some embodiments, the electrical stimulation is anodic stimulation (e.g., where the active electrode(s) are anodes), which is often more effective for selective stimulation of cell bodies than cathodic stimulation.

Producing a combination of stimulation regions 762 may facilitate effective stimulation of a relatively large part, or even all, of the NBM 760. The stimulation regions 762 illustrated in FIGS. 7 and 8 correspond to the estimated effective regions of stimulation for a particular set of stimulation parameters. Examples of stimulation parameters include, but are not limited to, selection of electrode(s), stimulation amplitude (which can be independent for each electrode), pulse frequency, pulse duration or width, or the like. In at least some embodiments, the stimulation regions 762 of FIGS. 7 and 8 can be determined or estimated algorithmically or manually. The terms "stimulation field map" (SFM), "volume of activation" (VOA), or "volume of tissue activated (VTA)" are often used to designate the estimated stimulation region 762 of tissue that will be stimulated for a particular set of stimulation parameters. Any suitable method for determining the VOA/SFM/VTA can be used including those described in, for example, U.S. Pat. Nos. 8,326,433; 8,675,945; 8,831,731; 8,849,632; and 8,958,615; U.S. Patent Application Publications Nos. 2009/0287272; 2009/0287273; 2012/0314924; 2013/0116744; 2014/0122379; 2015/0066111; 2016/0346557; 2016/0375248; 2016/0375258; 2017/0304633; 2018/0064930; 2018/0078776; 2018/0185650; 2018/0193655; 2019/0282820; 2019/0329049; 2019/0358458; 2019/0358461; and 2020/0289834 and U.S. Provisional Patent Application Ser. No. 62/030,655, all of which are incorporated herein by reference in their entireties.

In at least some embodiments, using electrodes of the same or different electrical stimulation leads, multiple stimulation regions 762 are chosen so that the combination of these stimulation regions can cover much of the target NBM 760. Any suitable number of stimulation regions 762 can be used including, but not limited to, one, two, three, four, five, six, eight, ten, twelve, or more stimulation regions. In at least some embodiments, the stimulation regions 762 may also be chosen to limit or avoid overlap between stimulation regions.

In at least some embodiments, the selection of multiple stimulation regions 762 (for example, SFMs) can be based on post-op radiography, an MIl, or any other imaging technique or any combination thereof. In at least some embodiments, the selection of multiple stimulation regions 762 (for example, SFMs) can be based on a surgical plan, alone or in combination with post-op imaging. In at least some embodiments, the selection of multiple stimulation regions 762 (for example, SFMs) is performed offline.

In at least some embodiments, the selection of multiple stimulation regions 762 (for example, SFMs) can be performed manually using a user interface of a programmer or other device that enables display of multiple stimulation regions simultaneously. In at least some embodiments, the selection of multiple stimulation regions 762 (for example, SFMs) can be performed algorithmically by using techniques, such as, for example, binary search, gradient descent searches, genetic or particle swarm searches, or the like or any combination thereof.

In at least some embodiments, the stimulation regions 762 are chosen based on scoring or other criteria that increases based on the amount of the NBM 760 is covered by the stimulation regions or penalizes for portions of the target NBM 760 that are not covered by the stimulation regions. In at least some embodiments, the stimulation regions 762 the scoring criteria penalizes for overlap between stimulation regions. In at least some embodiments, the scoring criteria may be weighted for the overlap or non-stimulation regions. Examples of scoring and scoring criteria can be found at, for example, U.S. Patent Application Publications Nos. 2016/0001080; 2014/0277284; 2014/0200633; 2014/0067022; 2014/0066999; 2013/0116929; 2013/0116748; 2013/0060305; and 2012/0271376, all of which are incorporated herein by reference in their entireties.

The delivery of electrical stimulation to the stimulation regions can include additional stimulation parameters beyond amplitude, pulse width, pulse frequency, and the like. Examples of additional stimulation parameters include, but are not limited to, duty cycle ratio, duration of a stimulation cycle, total number of pulses in a stimulation period, duration of a stimulation period, number of stimulation periods a day, or the like or any combination thereof. The delivery of stimulation to the stimulation region can be described in a series of cycles with stimulation during a portion of the cycle and no stimulation during another portion of the cycle. The duty cycle ratio can be equal to the ratio of the time during which stimulation is provided to the time during which no stimulation is provided. For example, a 60 second cycle may include 20 seconds of stimulation and 40 seconds of no stimulation resulting in a stimulation duty cycle ratio of 1:2. The duration of the cycle can be any suitable number including, but not limited to, 5, 10, 15, 20, 30, or 45 seconds or 1, 2, 5, 10, 15, 30, or 60 minutes or more, or the like. The duty cycle ratio can be any suitable ratio including, but not limited to, a ratio in a range from 1:5 to 5:1 or from 1:3 to 3:1 or from 1:5 to 1:1.

The stimulation period can be defined as the period of time when multiple cycles of stimulation are performed. The duration of the stimulation period can be any suitable number including, but not limited to, 1, 2, 5, 10, 15, 30, or 45 minutes or 1, 1.25, 1.5, 1.75, 2, 2.5, or 3 hours or more. In at least some embodiments, the duration of the stimulation period may be defined as a number of pulses instead or, or in addition to, a period of time. The number of pulses in a stimulation period can be any suitable number and, at least in some embodiments, can be in a range of 1,000 to 100,000 or in a range of 5,000 to 50,000 or in a range of 10,000 to 30,000.

The number of stimulation periods per day can be any suitable number including, but not limited to, one, two, three, four, five, six, eight, ten, twelve, 15, 20, or more. In at least some embodiments, the number of stimulation periods per day or the number or stimulation pulses delivered per day may be considered a "dose". As an example, stimulation to one of the stimulation regions 762 can be delivered at a pulse rate of 20 Hz during 20 seconds of a 60 second cycle (for a duty cycle ratio of 1:2) for a stimulation period of 60 minutes (i.e., 60 cycles) with one stimulation period per day (for a total of 24,000 stimulation pulses per day).

In at least some embodiments, the stimulation regions 762 are stimulated for the same or similar amounts of time during a cycle or a stimulation period. In other embodiments, there may be a different amount of stimulation time (e.g., different amount of time for a cycle or a stimulation period) for different stimulation regions 762.

When multiple stimulation regions 762 are to be stimulated, in at least some embodiments, the stimulation of each of the stimulation regions 762 can be performed using temporal offsets. In at least some embodiments, the delivery of stimulation may be interleaved. For example, one stimulation region can be stimulated followed by another and so on. For example, during a 60 second cycle stimulation is delivered to first stimulation region for 20 seconds, then to a second stimulation region for 20 seconds, and then to third stimulation region for 20 seconds. Thus, each stimulation region is stimulated at a duty cycle ratio of 1:2. In this example, overlap between the three stimulation regions is preferably relatively small or zero.

As another example, the cycles can be interleaved so that during the first 60 second cycle stimulation is delivered to first stimulation region for 20 seconds, then for a second 60 second cycle stimulation is delivered to a second stimulation region for 20 seconds, and then for a third 60 second cycle stimulation is delivered to third stimulation region for 20 seconds. In this example, overlap between the three stimulation regions may be less important because 40 seconds of each 60 second period has no stimulation at all.

In other embodiments, the stimulation periods for at least some stimulation regions 762 are performed sequentially. For example, during a first stimulation period the first stimulation region is stimulated, then for a second stimulation period the second stimulation region is stimulated, and then for a third stimulation period the third stimulation region is stimulated. For example, the first stimulation region can be stimulated for one three hour stimulation period, followed by the second stimulation region being stimulated for a second three hour stimulation period, and then followed by the third stimulation region being stimulated for a third stimulation period.

These arrangements avoid continual stimulation of the stimulation regions 762 as it is believed that periodic stimulation is more beneficial. In at least some embodiments, more than one stimulation region 762 can be stimulated at any given period of time and, preferably, stimulation regions 762 that are simultaneously stimulated do not overlap and are more preferably separated from each other by at least 0.1 to 1 millimeter.

In at least some embodiments, the delivery of stimulation may be performed automatically using stimulation settings programmed by a clinician or other caregiver. In at last some embodiments, the delivery of stimulation may be initiated manually by a patient, clinician, or other caregiver. In at least some embodiments, the automated delivery of stimulation may be supplemented or replaced by manual initiation of stimulation. In at least some embodiments, a system may limit the manual initiation of stimulation by a patient, clinician, or other caregiver to number of stimulation periods that can be delivered in a day, or a week, or other defined period of time.

In at least some embodiments, a patient, clinician, or other caregiver can initiate a bolus of therapeutic stimulation from an external device (such as RC 16 or CP 18) at a time that is convenient. In at least some embodiments, the electrical stimulation system 10 can be configured to only allow the patient to initiate a prescribed number of boluses per unit time (e.g., day or week). In at least some embodiments, the electrical stimulation system 10 includes an external device (such as RC 16 or CP 18) that when connected to the IPG 12 will reflect a warning if the patient has not initiated a predetermined or suitable number of therapy sessions. In at least some embodiments, this data or warning may be sent to a clinician or other caregiver, so that they can respond.

In at least some embodiments, the system or method allows the patient, clinician, or a caregiver the ability to postpone stimulation. In at least some embodiments, the system (for example, the IPG 14, RC 16, CP 18, or another device) may alert a patient, clinician, or caregiver that stimulation is being delivered or is about to be delivered using an external device (for example, RC 16, CP 18, a mobile phone, or the like). In at least some embodiments, the patient, clinician, or a caregiver can use the external device to postpone stimulation. In at least some embodiments, the external device includes at least one control that permits stimulation to be postponed for a period of time (for example, 1, 2, 5, 10, 15, 30, 45, or 90 minutes or 1, 2, 3, 4, 6, 9, 12, or 18 hours or 1 day or more or any other suitable period of time.)

In at least some embodiments, stimulation may have a detrimental effect on the memory or cognitive ability of the patient during the period of stimulation. In at least some embodiments, the electrical stimulation system 10 can be programmed to deliver stimulation at night (or other periods of time) when the patient is likely asleep. In at least some embodiments, the electrical stimulation system 10 or IPG 12 is configured to track the time of day and can be programmed to deliver stimulation at night (or other periods of time) when the patient is likely asleep. In at least some embodiments, the electrical stimulation system 10 or IPG 12 can be coupleable to an external or implantable sensor 40 (for example, a heart rate, respiration, posture, accelerometer, or biomarker sensor) or device that contains a sensor 40 (for example, a mobile phone or fitness tracker) that can provide information about the state of the patient to determine or estimate whether the patient is awake or asleep. The IPG 12 may be configured to provide stimulation only when the IPG or electrical stimulation system 10 determines (or receives information from an external sensor 40 or device that contains a sensor 40) that the patient is asleep. In at least some embodiments, the IPG 12 or electrical stimulation system 10 may determine, estimate, or receiving information from an external device regarding a sleep stage (for example, REM sleep) of the patient and provide stimulation only during one or more selected or specified sleep stages.

In some embodiments, the electrical stimulation system 10 or IPG 12 can be configured with "daytime" or "awake" stimulation parameters and with "nighttime" or "asleep" stimulation parameters, and can use a clock or any of the other approaches described above to determine which should be used when a period of stimulation is initiated.

In at least some embodiments, the detrimental effect on the memory or cognitive ability is reduced with cessation of stimulation and may improve over time after the cessation of stimulation. In at least some embodiments, the detrimental effect on the memory or cognitive ability of the patient during stimulation decreases over time. Although the methods and systems described herein are not dependent on any particular theory, it is thought that the brain or NBM may become more accustomed to stimulation over time. In at least some embodiments, cognitive performance concurrent with stimulation improves over an acclimation period (which may be 1, 2, 5, 7, 10, 14, 15, 21, 28, 30, 45, 60, 90, 120, or 180 days or 1, 2, 3, 4, 6, 8, 9, or 10 months or 1 year or more or any other suitable time period.) The acclimation period may vary between individuals, may vary with implantation site or arrangement, or may vary depending on the stimulation parameters or amount of stimulation, or the like or any combination thereof.

In at least some embodiments, the system or method can be configured to initially deliver stimulation during times when a cognitive load is not expected to be needed. The term "cognitive load" refers to period of time in which the patient is actively using their mental faculties and working memory including, but not limited to, periods of time in which the patient is performing tasks for work (professional or at home), recreation, or hobbies; driving; reading; teaching; learning; performing tasks that require mental focus; or the like. Instances in which a cognitive load is not expected to be needed include, but are not limited to, sleeping, resting, watching television, listening to music, or the like. In at least some embodiments, the patient, user, clinician, programmer, or any other suitable individual (or multiple individuals) can program the system to define what activities are not expected to need a cognitive load or what activities do need a cognitive load or any combination thereof.

In at least some embodiments, this behavior of the system or method can be change over time so that the stimulation can be delivered during times of cognitive load. In at least some embodiments, the change can be automatic or can be initiated manually or both options can be present. In at least some embodiments, the change can be gradual with increasing amounts of time during which the stimulation is delivered during times of cognitive load.

In at least some embodiments, the methods or systems can initially deliver a relatively low level of stimulation (e.g., a relatively low amplitude, a relatively low duration, or the like or any combination thereof.) In at least some embodiments, the relatively low level of stimulation can reduce or eliminate the detrimental effect on the memory or cognitive ability during stimulation. Over time, the level of stimulation can be increased or ramped up. For example, the amplitude, duration, or the like or any combination thereof can be increased or ramped up over time (for example, over a period of 1, 2, 5, 7, 10, 14, 15, 21, 28, 30, 45, 60, 90, 120, or 180 days or 1, 2, 3, 4, 6, 8, 9, or 10 months or 1 year or more or any other suitable time period.) In at least some embodiments, the final amplitude or final duration is at least 1.2, 1.5, 2, 3, 4, 5, 8, 10, 15, or 20 times larger than the initial amplitude or initial duration.

Although the methods and systems described herein are not dependent on any particular theory, it is thought that the brain can become accustomed to receiving stimulation during this period of increasing or ramping up stimulation. In at least some embodiments, parameters of the increase or ramp (for example, starting intensity or amplitude, ending intensity or amplitude, starting duration (e.g., a starting daily duration), ending duration (e.g., an ending daily duration), duration of the time period, the type of increase or ramp— such as linear, non-linear, stepped, exponential, or the like or any combination) can be selected or programmable by a clinician or other individual. In at least some embodiments, the ramp can include increasing intensity, increasing duration (e.g., increasing daily duration), or any combination thereof.

In at least some embodiments, a system or method can include or utilize one or more sensors 40 (FIG. 1) to detect when stimulation evokes a physiological response. Examples of suitable sensors 40 include, but are not limited to, a blood flow sensor (for example, an implantable or external blood flow sensor), an electrocorticography (ECoG) sensor (for example, an implantable ECoG sensor which can be implanted, for example, over the cortex at the time the lead is placed), an electroencephalography (EEG) sensor (for example, an external or implantable EEG sensor), a movement sensor (for example, at least one accelerometer, gyroscope, a chemical concentration sensor, an enzyme activity sensor, or the like or any combination thereof) which may be internal or on an external device (for example, a phone, watch, exercise monitor, or the like). A ECoG or EEG sensor can be used to detect changes in brain activity, such as alpha wave brain activity (for example, brain activity in the range of 8 to 12 Hz). A movement sensor can be used to detect changes in activity level, such as an increase or decrease of activity.

In at least some embodiments, the measurements of the sensor(s) 40 are used to determine or modify stimulation parameters, to aid in surgical implantation, or to aid in system programming. In at least some embodiments, the measurements of the sensor(s) 40 are used to modulate therapy for the patient (for example, to evoke a physiological response at a certain level, to evoke a physiological response a certain number of times per day or per specified period, to measure a rate of the response to determine or modify appropriate therapy, or the like or any combination thereof.)

In at least some embodiments, the implantable pulse generator (such as IPG 14) receives the measurements of the sensor(s) 40 and can determine or modify the stimulation parameters based on the measurements or modulate the therapy based on the measurements. In at least some embodiments, an external device (such as RC 16, CP 18, a mobile phone, a computer, or the like or any combination) receives the measurements of the sensor(s) and can determine or modify the stimulation parameters based on the measurements or modulate the therapy based on the measurements and then communicate the stimulation parameters or the modulate therapy to the implantable pulse generator.

Additionally or alternatively, optical stimulation of the NBM may be performed. In at least some embodiments, the delivery of light to the NBM may mitigate neurodegeneration. Examples of optical stimulation systems (at least some of which also produce electrical stimulation, e.g., electro-optical stimulation systems) with optical or electro-optical stimulation leads are found in, for example, U.S. Pat. No. 9,415,154 and U.S. Patent Application Publications Nos. 2013/0317573; 2017/0225007; 2017/0259078; 2018/0110971; 2018/0369606; 2018/0369608; 2020/0155854; and 2020/0376262, all of which are incorporated by reference in its entirety.

Figure 9:
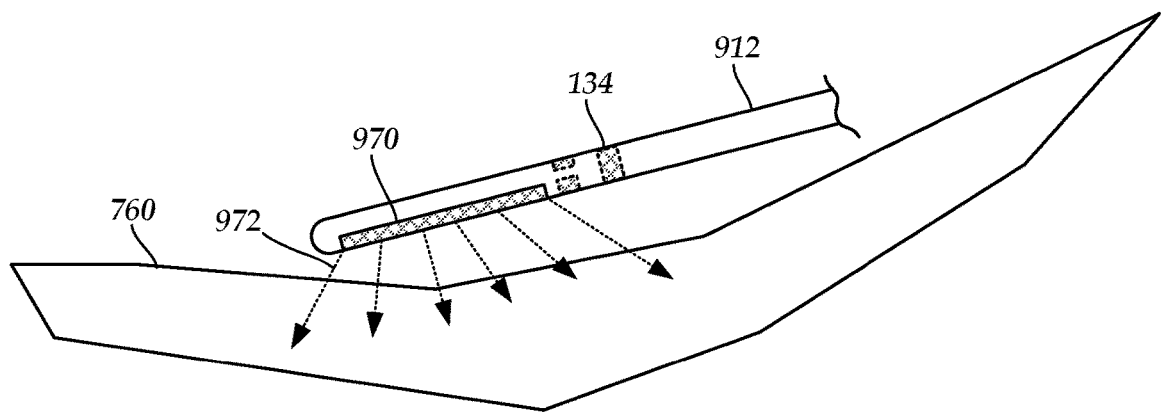
FIG. 9 is schematic side view of one embodiment of a method of stimulating the NBM using one optical (or electro-optical) stimulation lead implanted in a lateral-to-medial trajectory.
Figure 10:
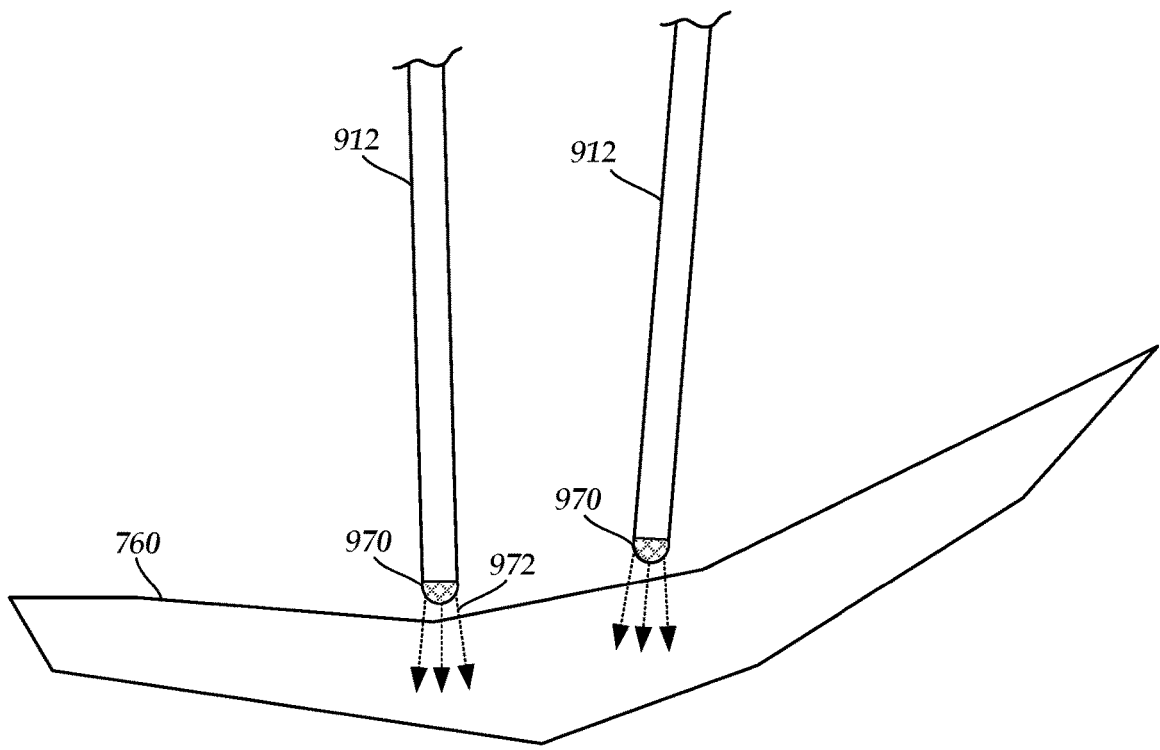
FIG. 10 is schematic side view of one embodiment of a method of stimulating the NBM using two optical stimulation leads.

FIGS. 9 and 10 illustrate optical stimulation leads 912 (or electro-optical lead in FIG. 9 with optional electrodes 134) with light delivery elements 970 that produce stimulation light 972 to stimulate the target NBM 760. The electrical stimulation components described above, and illustrated in FIGS. 1 to 6, can be used or adapted for use in optical or electro-optical stimulation systems, as further described in the references cited above.

Examples of light delivery elements 970 include, but are not limited to, light emitting diodes (LEDs), laser diodes, or a fiber optic coupled to a light source (such as an LED or laser diode). In FIG. 9, the light delivery element 970 can be a combination of multiple light delivery elements.

Any suitable number of leads 912 can be used to stimulate the NBM including, but not limited to, one, two, three, four, or more leads. When multiple leads 912 are used, there can be any suitable combination of lead(s) 912 implanted in the superior-to-inferior trajectory (FIG. 10) and lead(s) implanted in the lateral-to-medial trajectory (FIG. 9). Lead(s) 912 can be implanted in one or both hemispheres of the brain to stimulate one or both NBMs 760. The arrangement of lead(s) 912 for each hemisphere can be the same or different.

In at least some embodiments, the area of illumination by one or more light delivery elements 970 can be considered analogous to a stimulation region 762 for electrical stimulation. All of the features, additional parameters, and other options and considerations described above for electrical stimulation can be applied to optical stimulation. In at least some embodiments, the optical stimulation can be delivered in one or more stimulation periods per day for a duration of 1, 2, 5, 10, 15, 30, 60, or more minutes (or any other suitable duration) per stimulation period.

Any suitable wavelength, wavelength range, or combination of wavelengths can be emitted by the light delivery elements 970. In at least some embodiments, a lead 912 can include light delivery elements 970 that emit different wavelengths of light or are capable of delivering multiple wavelengths of light. In at least some embodiments, at least one of the light delivery elements 970 of a lead 912 is capable of emitting light having at least one wavelength in a range of 600 to 850 nm or in a range of 620 to 720 nm.

In at least some embodiments, a system is configured to deliver both optical and electrical stimulation using the same or different leads. For example, any combination of leads 12 and lead 912 can be used and any combination of lead trajectories.

In at least some embodiments, an electro-optical stimulation lead can include both electrode(s) 134 and light delivery element(s) 970. Examples of such leads are described in the references cited above. In at least some embodiments, the electrode(s) 12 and light deliver element(s) 912 are both powered by a common implantable power source (for example, power source 612 of FIG. 6). In other embodiments, the electrode(s) and light deliver element(s) are delivered using different leads coupled to different implantable power sources. The implantable power source(s) can be rechargeable or non-rechargeable.

In at least some embodiments, the electrical, optical, or combined stimulation system is powered transcutaneously via radiofrequency energy or some other external energy source (e.g., ultrasound).

Figure 11:
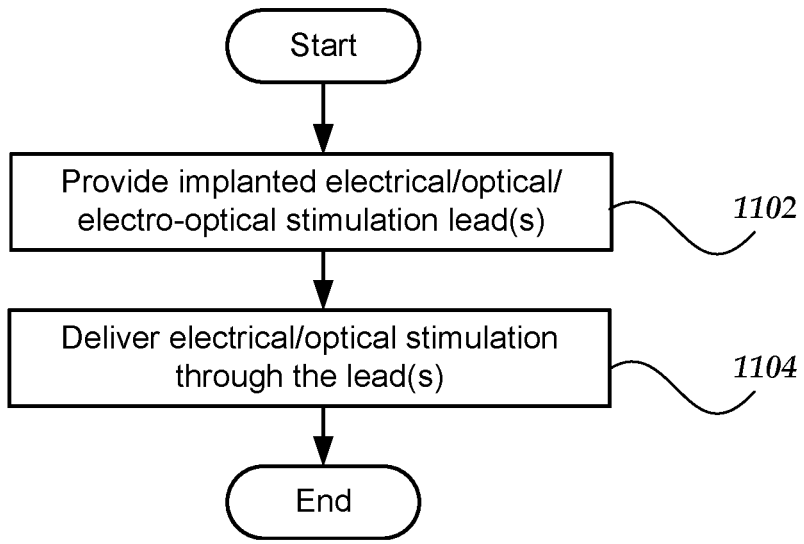
FIG. 11 is a flowchart of one embodiment of method of stimulating the NBM.

FIG. 11 is a flowchart of one embodiment of a method of stimulating the NBM. The objective of stimulation of the NBM can be to increase production or delivery of Ach, to reduce slow or halt degeneration of the neurons of the NBM, or the like or any combination thereof. In step 1102, one or more electrical stimulation lead, optical stimulation leads, electro-optical stimulation leads, or any combination thereof is implanted in or near the NBM. For example, an electrical stimulation lead or electro-optical stimulation lead may be implanted into the brain of the patient so that at least one or more of the electrodes are disposed in or near the NBM. As another example, an optical stimulation lead or electro-optical stimulation lead may be implanted into the brain of the patient so that at least one or more of the light delivery elements are disposed in or near the NBM. Following implantation, a programming process may be used to determine a set of stimulation parameters for the treatment as discussed above. The IPG may also be implanted. In at least some embodiments, the IPG is implanted in the torso with the lead, or a lead extension coupled to the lead, extending under the skin to the IPG. In at least some embodiments, the lead can be coupled instead to an ETS or other external stimulator.

In step 1104, electrical/optical stimulation is delivered through the lead to stimulate the NBM using the set of stimulation parameters. Methods, considerations, and examples of electrical/optical stimulation are described above.

One aspect is a method for stimulating the nucleus basalis of Meynert (NBM) that includes implanting an electrical stimulation lead in a lateral-to-medial trajectory into a brain of a patient, wherein the electrical stimulation lead includes electrodes and at least one of the electrodes is disposed adjacent to or within the NBM of the patient; and delivering electrical stimulation to the NBM through at least one of the electrodes.

In at least some aspects, the method further includes delivering optical stimulation to the NBM using at least one light delivery element of the electrical stimulation lead. In at least some aspects, the method further includes implanting an optical stimulation lead into the brain of the patient, wherein the optical stimulation lead includes at least one light delivery element disposed adjacent to or within the NBM of the patient and delivering optical stimulation to the NBM through at least one of the at least one light delivery elements.

Another aspect is a method for stimulating the nucleus basalis of Meynert (NBM) that includes implanting a plurality of electrical stimulation leads into a brain of a patient, wherein each of the electrical stimulation leads includes a plurality of electrodes and at least one of the electrodes of each of the electrical stimulation leads is disposed adjacent to or within the NBM of the patient; and, for each of a plurality of different stimulation regions of the NBM, delivering electrical stimulation through at least one of the electrodes, wherein the delivery of electrical stimulation to at least some of the stimulation regions is interleaved or sequential.

In at least some aspects, the implanting includes implanting at least one of the electrical stimulation leads in a superior-to-inferior trajectory. In at least some aspects, the implanting includes implanting at least one of the electrical stimulation leads in a lateral-to-medial trajectory.

Yet another aspect is a method for stimulating the nucleus basalis of Meynert (NBM) that includes implanting either a) at least one electro-optical stimulation lead into a brain of a patient or b) at least one electrical stimulation lead and at least one optical stimulation lead into the brain of the patient, wherein each electrical stimulation lead or electro-optical stimulation lead includes at least one electrode with at least one of the at least one electrode disposed adjacent to or within the NBM of the patient and each optical stimulation lead or electro-optical stimulation lead includes at least one light delivery element with at least one of the at least one light delivery element disposed adjacent to or within the NBM of the patient; delivering electrical stimulation to the NBM through at least one of the electrodes; and delivering optical stimulation to the NBM through at least one of the at least one light delivery element.

In at least some aspects, the implanting includes implanting at least one of the at least one electro-optical stimulation lead or the at least one optical stimulation lead in a superior-to-inferior trajectory. In at least some aspects, the implanting includes implanting at least one of the at least one electro-optical stimulation lead or the at least one optical stimulation lead in a lateral-to-medial trajectory.

In at least some aspects, delivering electrical or optical stimulation includes delivering the electrical or optical stimulation to the NBM to stimulate neurons of the NBM to deliver more acetylcholine or to support survival of neurons of the NBM so that they can perform the neuron's function, including delivery of acetylcholine to the cortex. In at least some aspects, the electrodes of the electrical or electro-optical stimulation lead include at least one set of segmented electrodes disposed around a circumference of the electrical or electro-optical stimulation lead.

In at least some aspects, delivering electrical stimulation includes delivering electrical stimulation to a plurality of stimulation regions of the NBM at different periods of time. In at least some aspects, the method further includes selecting the plurality of stimulation regions so that each stimulation region covers a portion of the NBM. In at least some aspects, the selecting includes selecting the plurality of stimulation regions using scoring criteria that promote covering more of the NBM and penalize overlap of the stimulation regions. In at least some aspects, the method further includes determining each of the stimulation regions algorithmically as an estimated volume of effective region of stimulation for a particular set of stimulation parameters.

In at least some aspects, delivering electrical stimulation includes delivering anodic stimulation to the NBM.

In at least some aspects, delivering electrical or optical stimulation includes delivering electrical or optical stimulation when the patient is estimated to be asleep. In at least some aspects, delivering electrical or optical stimulation when the patient is estimated to be asleep includes estimating that the patient is asleep based on a clock in an implantable pulse generator coupled to electrical or optical stimulation lead or in an external device in communication with the electrical or optical stimulation lead or the implantable pulse generator. In at least some aspects, delivering electrical or optical stimulation when the patient is estimated to be asleep includes estimating that the patient is asleep based on a measurement or indication from an external sensor or external device that is in communication with an implantable pulse generator coupled to electrical or optical stimulation lead.

In at least some aspects, delivering electrical stimulation includes delivering electrical or optical stimulation when the patient or another directs the delivery.

It will be understood that each block of the flowchart illustration, and combinations of blocks in the flowchart illustration and methods disclosed herein, can be implemented by computer program instructions. In addition, the feature extraction engine, storage engine, visualization engine, and storage programming engine may be implemented by computer program instructions. These program instructions may be provided to a processor to produce a machine or engine, such that the instructions, which execute on the processor, create means for implementing the actions specified in the flowchart block or blocks or engine disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computing device. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device. The computer program instructions can be stored locally or nonlocally (for example, in the Cloud).

The above specification and examples provide a description of the arrangement and use of the invention. Since many embodiments of the invention can be made without departing from the spirit and scope of the invention, the invention also resides in the claims hereinafter appended.

What is claimed as new and desired to be protected is:
1. A method for stimulating a nucleus basalis of Meynert (NBM) of a patient, the method comprising:
   implanting an electrical stimulation lead in a brain of the patient, wherein the electrical stimulation lead com- prises a plurality of electrodes and at least one of the electrodes is disposed adjacent to or within the NBM of the patient; and delivering electrical stimulation to the NBM through at least one of the electrodes, wherein during an initial stimulation period, which is at least 1 month in duration, the electrical stimulation is not delivered during periods in which a cognitive load for the patient is expected.

2. The method of claim 1, further comprising, prior to, or during, delivery of the electrical stimulation, indicating to a user that the electrical stimulation is being delivered or soon to be delivered.

3. The method of claim 2, further comprising, in response to user operation of a postponement control, postponing the delivery of the electrical stimulation.

4. The method of claim 1, further comprising, after the initial stimulation period, increasing, over time, an amount of daily time during which the electrical stimulation is delivered during the periods in which the cognitive load for the patient is expected.

5. The method of claim 1, further comprising, during the initial stimulation period, increasing over time of an amplitude of the electrical stimulation from an initial value at a start of the initial stimulation period to a final value at an end of the initial stimulation period.

6. The method of claim 5, wherein the increasing comprises increasing over time the amplitude from the initial value to the final value according to a linear ramp.

7. The method of claim 5, wherein the increasing comprises increasing over time the amplitude from the initial value to the final value according to a non-linear ramp.

8. The method of claim 1, further comprising monitoring the patient using a sensor selected from a blood flow sensor, an electroencephalography (EEG) sensor, an electrocorticography (ECoG) sensor, a movement sensor, a chemical concentration sensor, an enzyme activity sensor, or any combination thereof.

9. The method of claim 8, wherein monitoring the patient comprises monitoring alpha wave brain activity of the patient using the EEG or ECOG sensor.

10. The method of claim 1, further comprising, during the initial stimulation period, increasing over time of a duration of the electrical stimulation from an initial value at a start of the initial stimulation period to a final value at an end of the initial stimulation period.

11. The method of claim 10, wherein the increasing comprises increasing over time the at least one of the duration from the initial value to the final value according to a linear ramp.

12. The method of claim 10, wherein the increasing comprises increasing over time the at least one of the duration from the initial value to the final value according to a non-linear ramp.

13. The method of claim 1, wherein delivering the electrical stimulation comprises, after the initial stimulation period and during a second stimulation period, increasing, over time, an amount of time during which the electrical stimulation is delivered during periods in which cognitive load for the patient is expected.

14. The method of claim 3, further comprising sending a warning when stimulation has not been initiated a predetermined number of electrical stimulation sessions over a predetermined period of time.

15. The method of claim 1, wherein implanting the electrical stimulation lead comprises implanting the electrical stimulation lead in a trajectory oriented within 15 degrees of lateral-to-medial into a brain of a patient.

16. The method of claim 1, wherein delivering electrical stimulation comprises delivering the electrical stimulation to the NBM to stimulate neurons of the NBM to deliver more acetylcholine.

17. The method of claim 1, wherein delivering electrical stimulation comprises delivering electrical stimulation to a plurality of stimulation regions of the NBM with the delivery of electrical stimulation to different ones of the stimulation regions occurring at different periods of time.

18. The method of claim 17, further comprising selecting the plurality of stimulation regions so that each stimulation region covers a portion of the NBM.

19. The method of claim 17, further comprising determining each of the stimulation regions algorithmically as an estimated volume of effective region of stimulation for a particular set of stimulation parameters.

20. The method of claim 1, further comprising delivering optical stimulation to the NBM using at least one light delivery element of the electrical stimulation lead.

* * * * *